US010694692B2

(12) United States Patent
Li et al.

(10) Patent No.: US 10,694,692 B2
(45) Date of Patent: Jun. 30, 2020

(54) PLANT VARIETIES BY APPLICATION OF ENDOCIDES

(71) Applicant: Stephen F. Austin State University, Nacogdoches, TX (US)

(72) Inventors: Shiyou Li, Nacogdoches, TX (US); Ping Wang, Nacogdoches, TX (US); Zushang Su, Nacogdoches, TX (US)

(73) Assignee: Stephen F. Austin State University, Nacogdoches, TX (US)

( * ) Notice: Subject to any disclaimer, the term of this patent is extended or adjusted under 35 U.S.C. 154(b) by 0 days.

(21) Appl. No.: 15/775,570

(22) PCT Filed: Nov. 10, 2016

(86) PCT No.: PCT/US2016/061283
§ 371 (c)(1),
(2) Date: May 11, 2018

(87) PCT Pub. No.: WO2017/083490
PCT Pub. Date: May 18, 2017

(65) Prior Publication Data
US 2018/0352763 A1 Dec. 13, 2018

Related U.S. Application Data

(60) Provisional application No. 62/253,965, filed on Nov. 11, 2015.

(51) Int. Cl.
*A01H 1/06* (2006.01)
*C05G 3/00* (2020.01)
*A01N 43/40* (2006.01)
*A01N 37/40* (2006.01)

(52) U.S. Cl.
CPC .............. *A01H 1/06* (2013.01); *A01N 37/40* (2013.01); *A01N 43/40* (2013.01); *C05G 3/00* (2013.01)

(58) Field of Classification Search
None
See application file for complete search history.

(56) References Cited

U.S. PATENT DOCUMENTS

| 3,671,213 A | 6/1972 | White et al. |
| PP11,959 P2 | 6/2001 | Li |
| 9,918,480 B2 | 3/2018 | Li et al. |
| 2007/0264369 A1 | 11/2007 | Moon |

FOREIGN PATENT DOCUMENTS

| WO | WO 02/42428 | 5/2002 |
| WO | WO 2014133811 A2 * | 9/2014 |
| WO | WO 2014/182627 | 11/2014 |
| WO | WO 2014/182627 A1 * | 11/2014 |

OTHER PUBLICATIONS

Li et al., 2010, Induced exogenous activity in Camptotheca, Frontiers in Bioscience E2, 1196-1210.*
Wu et al., 2007, Autotoxicity of wheat (Triticum aestivum L.) as determined by laboratory bioassays, Plant Soil 296: 85-93.*
Zhang et al., 2004, Fern allelopathy and its impact on biodiversity, Biodiversity Science 12: 466-471.*
Singh et al., 1999, Autotoxicity: Concept, Organisms, and Ecological Significance, Critical Reviews in Plant Sciences 18: 757-772.*
Choudhary et al., 2008, Phenolic and other constituents of fresh water fern Salvinia molesta, Phytochemistry 69: 1018-1023.*
Al-Sherif et al., 2013, Allelopathic effect of black mustard tissues and root exudates on some crops and weeds, Planta daninha vol. 31 No. 1: 11-19.*
Abad & Bermejo, "Bioactive Natural Products from Marine Sources," *Studies in Natural Products Chemistry*, Atta-ur-Rahman. Oxford, ElseVier. 25: 683-756, 2001.
Ali, et al., "Phytochemical, Pharmacological and Toxicological Aspects of Hibiscus Sabdariffa L.: A Review." *Phytotherapy Research*, 19(5): 369-375, 2005.
Asao, et al., "Autotoxicity of Root Exudates from Taro." *Scientia Horiculturae*, 97(3-4): 389-396, 2003.
Asao, et al., "Search of Autotoxic Substances in Some Leaf Vegetables." *Journal of the Japanese Society for Horticulture Science*, 73(3): 247-249, 2004.
Baldwin & Callahan, "Autotoxicity and Chemical Defense: Nicotine Accumulation and Carbon Gain in Solanaceous Plants." *Oecologia*. 94: 534-541, 1993.
Baldwin, "An Ecologically Motivated Analysis of Plant-Herbivore Interactions in Native Tobacco." *Plant Physiology*. 127(4): 1449-1458, 2001.
Bennett & Wallsgrove, "Secondary Metabolites in Plant Defence Mechanisms." *New Physiology*. 127: 617-633, 1994.
Bu'Lock, J.D. "OIigins of Secondary Metabolism" *Secondary Metabolites: Their Function and Evolution*. Wiley, Chichester (Ciba Foundation Symposium 171), 299-304, 1992.
Cavalier-Smith, "Origins of Secondary Metabolism," 1992 *Secondary Metabolites: Their Function and Evolution*. Wiley, 294 (Ciba Foundation Symposium 171), 64-87, 1992.
Croteau, et al., "Natural Products (Secondary Metabolites)," *Biochemistry and Molecular Biology of Plants, American Society of Plant Physiologists*. 1250-1318, 2000.
Dai, "Studies on the Interaction of Autotoxic Chemicals of Taizishen and the Microbes in Rhizosphere Soils," Proceeding of the 4th Symposium of the Committee of Resource ecology of Chinese Traditional Medicine of the Ecological Society of China and the Symposium of Committee of Traditional Chinese Medicine, 2012. (English Abstract).
Davies, et al., "Evolution of Secondary Metabolite Production: Potential Roles for Antibiotics as Prebiotic Effectors of Catalytic RNA Reactions," 1992 *Secondary Metabolites: Their Function and Evolution*. Wiley, Chichester (Ciba Foundation Symposium 171), 24-44, 1992.

(Continued)

*Primary Examiner* — Bratislav Stankovic
(74) *Attorney, Agent, or Firm* — Norton Rose Fulbright US LLP

(57) ABSTRACT

The present invention relates generally to compositions and methods for mutating a plant and plants and plant products produced by said methods. Also, compositions and methods for controlling a plant species are disclosed herein.

14 Claims, 11 Drawing Sheets

(56) References Cited

OTHER PUBLICATIONS

Demain, "Microbial Secondary Metabolism: A New Theoretical Frontier for Academia. A New Opportunity for Industry," 1992 *Secondary Metabolites: Their Function and Evolution.* Wiley, Chichester (Ciba Foundation Symposium 171), 3-23, 1992.
Dixon, "Natural Products and Plant Disease Resistance." *Nature.* 411: 843-847, 2001.
Ellnain-Wojtaszek, "Phenolic Acids from Ginkgo Biloba L. Part 11. Quantitative Analysis of Free and Liberated by Hydrolysis Phenolic Acids," *Acta Poloniae Pharmaceutica.* 54(3): 229-232, 1997.
Ffolliott, et al., "Pretreatment of Seeds" in *Dryland Forestry Planning and Management*, pp. 204-206, New York, Chichester, Brisbane, Toronto, Singapore, John Wiley & Sons, Inc., 1995.
Gog, et al., "Autotoxic Effects of Essential Oils on Photosynthesis in Parsley, Parsnip, and Rough Lemon." *Chemoecology*, 15: 115-119, 2005.
Herrmann, "Occurrence and Content of Hydroxycinnamic and Hydroxybenzoic Acid Compounds in Foods." *Critical Reviews in Food Science and Nutrition.* 28(4): 315-347, 1989.
Huang, et al., "Identification Ofautotoxins in Rhizosphere Soils Under the Continuous Cropping of Cowpea." *Allelopathy Journal*, 25(2): 383-392, 2010.
Huang, et al., "Plant-Soil Feedbacks and Soil Sickness: from Mechanisms to Application in Agriculture," *Journal of Chemical Ecology*, 39: 232-242, 2013.
Hudson, et al., "Characterization of Potentially Chemopreventive Phenols in Extracts of Brown Rice That Inhibit the Growth of Human Breast and Colon Cancer Cells." *Cancer Epidemiology Biomarkers and Prevention.* 9(11): 1163-1170, 2000.
Ibanez, et al., "Rapid Metabolic Profiling of Nicotiana Tabacum Defence Responses Against Phytophthora Nicotianae Using Direct Infrared Laser Desorption Ionization Mass Spectrometry and Principal Component Analysis." *Plant Methods.* 6: 14, 2010.
International Preliminary Report on Patentability Issued in Corresponding PCT Application No. PCT/US2016/061283, dated May 15, 2018.
International Search Report and Written Opinion Issued in Corresponding PCT Application No. PCT/US2016/61283, dated Jan. 24, 2017.
Jurgenliemk, et al., "Phenolic Compounds from Hypericum perforatum." *PlantaMedica.* 68(1): 88-91, 2002.
Kakkar &Bais, "A Review on Protocatechuic Acid and Its Pharmacological Potential." *ISRN Pharmacology,*: 1-9, 2014.
Kayano, S. I., H. Kikuzaki, et al. (2002). "Antioxidant Activity of Prune (Prunus domestica L.) Constituents and a New Synergist." *Journal of Agricultural and Food Chemistry.* 50(13): 3708-3712, 2012.
Kim, et al., "Phytotoxic Effects and Chemical Analysis of Leaf Extracts from Three Phytolaccaceae Species in South Korea." *Journal Chemical Ecology*, 31(5): 1175-1186, 2005.
Kliebenstein, et al., "Secondary Metabolites and Plant/Environment Interactions: A View Through *Arabidopsis Thaliana* Tinged Glasses." *Plant, Cell & Environment.* 27(6): 675-684, 2004.
Li, et al., "Camptothecin Accumulation and Variation in Camptotheca." *Planta Afedica.* 68(11): 1010-1016, 2002.
Li, et al., "High Performance Liquid Chromatographic Determination of Phenolic Acids in Fruits and Vegetables." *Biomedical and Environmental Sciences.* 6(4): 389-398, 1993.
Li, et al., "Identification of Autotoxic Compounds in Fibrous Roots of Rehmannia (Rehmannia glutinosa Libosch)." *PLoS ONE.* 7(1): e28806, 2012.
Li, et al., "Induced Endogenous Autotoxicity in Camptotheca." *Frontiers in Bioscience.* E2: 1196-1210, 2010.
Li, et al., "Taxonomy of Camptotheca Decaisne." *Pharmaceutical Crops.* 5 (Suppl 2: M2): 89-99, 2014.
Li, et al., "Trichome Management to Enhance Camptothecins in Camptotheca Decaisne." *Pharm. Crops.* 5(Suppl 2: M8): 146-162, 2014.
Li, et al., "A System for Increasing the Production of Indole and Quinoline Alkaloids, Particularly Camptothecins and Related Compounds From Plants," *R.O. China Invention.* 162720, 2002.
Li, et al., "Synergistic Rehmannia in Consecutive Effect of Autotoxins and Phytopathogenic Fungi on the Pathogenicity to Monoculture System", Fujian Univ. Agric. For., 2012. (English Abstract).
Li, et. Al., "Cytotoxic Compounds from Invasive Giant SalVinia(Sal Vinia Molesta) Against Human Tumor Cells." *Bioorganic & Medicinal Chemistry Letters.* 23(24): 6682-6687 2013.
Liu, et al., "Effects of Phenolic Acids and Amino Acid on the Growth of Fusarium Oxysporium F. Sp. Niveum." *Huibei Agric. Sci.* 50(20): 4180-4184, 2011. (English Abstract).
Liu, et al., "In Vivo Protective Effect of Protocatechuic Acid on Tertbutyl Hydroperoxide-Induced Rat Hepatoxicity," *Food and Chemical Toxicology*, 40(5): 635-641, 2002.
Liu, et al., "Interactive Effects of Three Kinds of Phenolic Acids on Peanut Germination and Soil Microbes." *Acta Agric. Jiangxi.* 24(8): 85-87,93, 2012.
Mandal, et al., "Phenolic Acids Act as Signaling Molecules in Plant-Microbe Symbioses." *Plant Signaling & Behavior.* 5(4): 359-368, 2010.
Masella, et al., "Antioxidant Activity of 3,4-DHPEA-EA and Protocatecuic Acid: A Comparative Assessment with Other Olive Oil Biophenols." *Redox Report.* 4(3): 113-121, 1999.
Mattila & Hellstrom, "Phenolic Acids in Potatoes, Vegetables, and Some of Their Products." *Journal of Food Composition and Analysis.* 20(3-4): 152-160, 2007.
Moorman, et al., "Production of Hydroxybenzoic Acids by Bradyrhizobium Japonicum Strains After Treatment with Glyphosate." *Journal of Agricultural and Food Chemistry.* 40: 289-293, 1992.
Netzly, et al., "Germination Stimulants of Witchweed (Striga Asiatica) from Hydrophobic Root Exudate of Sorghum (Sorghum bi color)." *Weed Science.* 36(441-446): 36, 1988.
Pacheco-Palencia, et al.,. "Chemical Composition, Antioxidant Properties, and Thermal Stability of a Phytochemical Enriched Oil from Acai (Euterpe oleracea Mart)." *Journal of Agricultural and Food Chemistry.* 56(12): 4631-4636, 2008.
Piepersberg, W. "Metabolism and Cell Individualization in Final Discussion" *Secondary Metabolites: Their Function and Evolution.* Wiley, Chichester (Ciba Foundation Symposium 171), 294-299, 1992.
Reisman-Berman, et al., "Short Soaking in Water Inhibits Germination of Daturaferox L. and D. stramonium L. Seeds," *Weeds Research.* 29: 357-363, 1989.
Rhoades, How to Soak Seeds Before Planting and the Reasons for Soaking Seeds, 2015. Accessed at http://www.gardeningknowhow.com.
Rinehart, "Secondary Metabolites from Marine Organisms," 1992 *Secondary Metabolites: Their Function and Evolution.* Wiley, Chichester (Ciba Foundation Symposium 171), 236-254, 1992.
Sang, et al.,. "Antioxidative Phenolic Compounds Isolated from Almond Skins (Prunus Amygdalus Batsch)," *Journal of Agricultural and Food Chemistry.* 50(8): 2459-2463, 2002.
Singh & Rajini, "Antioxidant-Mediated Protective Effect of Potato Peel Extract in Erythrocytes Against Oxidative Damage." *Chemico-Biological Interactions.* 173(2): 97-104, 2008.
Sirikantaramas, et al., "Mechanism of Resistance to Self-Produced Toxic Secondary Metabolites in Plants." *Phytochemistry Reviews.* 7: 467-477, 2008.
Sirikantaramas, et al., "Mutations in Topisomerase I as a Self-Resistance Mechanism Coevolved with the Production of the Anticancer Alkaloid Camptothecin in Plants." *PNAS.* 105: 6782-6786, 2008.
Wang, et al., "Effect of Phenolic Acid on the Root Growth and Photosynthetic Characteristics of Tobacco Seedling Characteristic Tobacco Seedling." *Guangdong Agricultural* Sciences (2): 14-18, 2014. (English Abstract).
Wang, J. C. (1996). "DNA Topoisomerases." *Annual Review of Biochemistry.* 65: 635-692, 1996.
Waterman, "Roles for Secondary Metabolites," 1992 *Secondary Metabolites: Their Function and Evolution.* Wiley, Chichester (Ciba Foundation Symposium 171), 255-275, 1992.

(56) References Cited

OTHER PUBLICATIONS

Williams & Maplestone, "Why are Secondary Metabolites Biosynthesized? Sophistication in the Inhibition of Cell Wall Biosynthesis by Vancomycin Group Antibiotics," 1992 *Secondary Metabolites: Their Function and Evolution*. Wiley, Chichester (Ciba Foundation Symposium 171), 45-63, 1992.
Williams, et al., "Why Are Secondary Metabolites (Natural Products) Biosynthesized?" *Journal of Natural Products*. 52(6): 1189-1208, 1989.
Wink, "Evolution of Secondary Metabolites from an Ecological and Molecular Phylogenetic Perspective." *Phytochemistry*. 64: 3-19, 2003.
Wu, et al., "The Phenolic, 3,4-Dihydroxybenoic Acid, is an Endogenous Regulator of Rooting in Protea Cynaroides." *Plant Growth Regulation*. 52: 207-215, 2007, accessed on web at https://repository.up.ac.za/bitstream/handle/2263/5576/Wu_Phenolic%282007%29.pdf?sequence=1.
Wu, H. C. (2006). "Improving in Vitro Propagation of Rooting in Protea Cynaroides L. (King Protea) and the Roles of Starch and Phenolic Compounds in the Rooting of Cuttings" PhD, University of Pretoria, Pretoria.
Young, J. & Young, C. (1992). *Seeds of Woody Plants in North America.—Revised and enlarged edition*. Portland, Or.; Dioscorides Press.
Yu, et al., "Effects of Allelochemicals from Tobacco Root Exudates on Seed Germination and Seedling Growth of Tobacco." *Allelopathy Journal*, 33(1): 107-120, 2014.
Yu, et al., "The Changes and Degradation of Tobacco Root Exudates in Tobacco Field with Continuous Cropping." *Chinese Tobacco Science*. 35(1): 43-47, 2014. (English Abstract).
Zeng, "Allelopathy—The Solution is Indirect." *Journal of Chemical Ecology*. 40: 515-516, 2014.
Zhang, et al., "Phenolic Acid in Nicotiana Tobacco L. Root Exudate and Their Autotoxicity Effects." *Southwest China Journal of Agricultural Sciences*, 26(6): 2552-2557, 2013. (English Translation).
Zhou, et al., "P-Coumaric Acid Influenced Cucumber Rhizosphere Soil Microbial Communities and the Growth of Fusarium Oxysporum F Sp. Cucumerinum Owen." *PLOS ONE*. 7 (10): e48288, 2012.
Zhou, et al., "Responses of Soil Microbial Communities in the Rhizosphere of Cucumber (Cucumis Sativus L.) to Exogenously Applied P-Hydroxybenzoic Acid." *Journal of Chemical Ecology* 38: 975-983, 2012.

\* cited by examiner

PLANT VARIETIES BY APPLICATION OF ENDOCIDES

CROSS-REFERENCE TO RELATED APPLICATIONS

This application is a national phase application under 35 U.S.C. § 371 of International Application No. PCT/US2016/061283, filed Nov. 10, 2016 which claims the benefit of priority of U.S. Provisional Patent Application No. 62/253,965, filed Nov. 11, 2015, each of which is hereby incorporated by reference in its entirety without disclaimer.

STATEMENT REGARDING FEDERALLY SPONSORED RESEARCH OR DEVELOPMENT

This invention was made with government support under grant number 2008-38928-19308 awarded by the U.S. Department of Agriculture. The government has certain rights in this invention.

BACKGROUND OF THE INVENTION

A. Field of the Invention

The present invention relates generally to the fields of biology, agriculture, and chemistry. More particularly, it concerns compositions and methods for inducing mutations in organisms and/or controlling the organisms.

B. Description of Related Art

Secondary metabolites, also known as natural products, are organic compounds that are not directly involved in the normal growth, development, and reproduction of an organism (Croteau et al., 2000; Dixon, 2001; Ibáñez et al., 2010). Secondary metabolites are substances appearing to have no explicit role in the internal economy of the producing organism (Williams et al., 1989), and it is commonly believed that they are responsible for interactions between the producing organism and its environment, particularly in defense (Davies, 1992; Bennett et al., 1994; Croteau et al., 2000; Abad et al., 2001; Baldwin, 2001; Dixon, 2001; Wink, 2003; Kliebenstein, 2004).

It has been widely believed that a species can avoid self-toxicity by its endogenous cytotoxic secondary metabolites (Baldwin et al., 1993; Wang, 1996; Gog et al., 2005; Sirikantaramas et al., *Phytochem* 2008; Sirikantaramas et al., *PNAS* 2008). As a result, studies in autotoxicity have primarily been focused on organisms' avoidance and detoxification mechanisms. Extracellular excretion, vacuolar sequestration, vesicle transport, extracellular biosynthesis, target mutations, and accumulation of metabolite in a non-toxic form, have all been proposed as methods of avoiding or mitigating the effects of endogenous toxic metabolites (Sirikantaramas et al., *Phytochem* 2008; Sirikantaramas et al., *PNAS* 2008).

The inventor previously reported that endocides from a species or a closely related species can be used to control organisms of that species or a closely related species by application of the endocide (PCT/US2014/036837). Also, the inventor previously reported that decapitation pruning can induce increased production of endogenous toxic camptothecin, a known mutagen that is not species specific, in *Camptotheca acuminata* Decaisne (Nyssaceae) (Li et al., 2010). The increased production of camptothecin correlates with endogenous autotoxicity and dramatic deviations from normal morphogenesis, including serrated or lobed leaves, disturbed phyllotaxis, and fasciated stems (Li et al., 2010). The inventor also found that decapitation pruning can enhance the concentration of naturally-occurring indole and quinolone alkaloids in *Camptotheca* (WO 02/42428). In these publications, the inventor described the morphological characteristics of the mutant cultivar *C. lowreyana* 'CT168' but did not describe the origin of mutation or development method of such a cultivar. Pruning has long been a known technique to promote lateral growth in plants, but to date, there is no reported pruning technology suggested to develop a new plant variety. Further, to date, there is no pruning technology suggested to develop mutations correlated with increased endogenous concentrations of endocides with mutational activities that are specific for one species and/or other closely related species.

Soaking seeds in water before planting has been a common practice to promote germination. It is recommended to soak seeds in water for 12 to 24 h and no more than 48 h (Young, 1992; Rhoaders, 2015) or 1 to several days for some tree and shrub species (Ffolliott et al., 1995). In contrast, some researchers found that soaking seeds in water inhibits germination in some species because water becomes trapped in tissues between the embryo and seed coat, creating an oxygen barrier (Reisman-Berman et al., 1989). Because current application of soaking seeds in water is to seek optimal germination, prolonged soaking time in water (e.g., several weeks) is always avoided.

Other compounds, such as phenolic acids, have also been reported to have inhibitory effects on seed germination and plant growth of some plant species. However, their role in inducing mutations, particularly in producing organisms, has never been reported. In the last decade, the primary research interest of phenolic acids has been focused on their allelopathic effects on plants, but some claimed "autotoxins" or "allelochemicals" are not necessarily responsible for toxicity observed in nature. Some of the reported activities are inconsistent or may be caused instead by the compound changing the environment of the plant. Recently, more investigators agree that the known autotoxicity phenomenon is primarily caused by the indirect effects of autotoxins via influencing microbes or parasitic organisms in the environment (Netzly, Riopel et al. 1988; Zhou and Wu 2012; Huang, Song et al. 2013; Zeng 2014).

SUMMARY OF THE INVENTION

The inventor has determined that modifications of the growth can selectively be induced in a species. Disclosed herein are compositions and methods to modify the growth of an organism by one or more endocide or derivative or analog thereof, to the organism or closely-related organisms. In some aspects, disclosed herein are methods and compositions for inducing mutations in producing or closely-related organisms by endocides. Mutations may be induced by pruning, decapitation pruning, fragmenting, by prolonged soaking of propagules in water, and by the application of endocides or secondary metabolites to the plant and/or propagules. Also disclosed herein are compositions and methods to control an organism by application of one or more endocide, derivative thereof, or analog thereof, to the organism. In some instances, the endocide is 4-hydroxybenzoic acid, 3,4-dihydroxybenzoic acid, derivatives thereof, analogs thereof, or a combination thereof. In some instances, the organism being controlled is in the order of Salviniales. In some instances, the organism is from the *Salvinia molesta* and/or *Azolla caroliniana* species.

Unlike some known mutagens with broad toxicity, some endocides induce mutations selectively in a species and its closely related species with little to no effects on non-closely related species. This selectivity is similar to that which was observed in control of the producing and closely-related species by endocides at higher dosages.

In one aspect, there is disclosed a method of modifying the growth of a plant of a first species. The growth can be modified by at least one endocide to the first species, a derivative thereof, and/or an analogue thereof, wherein the endocide is derived from the first species and/or a second closely related species, and wherein the growth of the plant is modified.

In one aspect, there is disclosed a method of producing a mutation in a plant of a first species, the method comprising contacting a propagule or other propagative tissue of a plant of the first species with a composition comprising at least one endocide to the first species, a derivative thereof, and/or an analogue thereof, wherein the endocide, derivative thereof, and/or analogue thereof is derived from the first species and/or a second closely related species, and wherein a mutation is induced. The amount of time the propagule or other propagative tissue is contacted with the composition can vary (e.g., amounts can be as low as 10 minutes to as high as 1 year or any range therein). In some instances, the method includes wherein the propagule or other propagative tissue is contacted with the composition for at least 12 hours, 24 hours, 48 hours, 1 week, 2 weeks, 4 weeks, 6 weeks, 8 weeks, 10 weeks, or 12 weeks. In some instances, the method includes wherein the propagule or other propagative tissue is contacted with the composition for less than 12 hours, 24 hours, 48 hours, 1 week, 2 weeks, 4 weeks, 6 weeks, 8 weeks, 10 weeks, or 12 weeks.

The mutations induced by the methods and compositions disclosed herein can include any mutation. In some instances, the method includes wherein the mutation produced causes shrubbiness, dwarfism, pleiocotyly, abnormal leaf morphogenesis, small leaves, disturbed phyllotaxis or fasciated stems, variegation, modification in chemical biosynthesis, and/or derivatization of a chemical naturally found in a non-mutated plant of the first species. In some instances, the method includes wherein the mutation is found in the whole plant and/or at least one part of the plant.

In some instances, any one of the methods disclosed herein includes wherein the endocide is from, or is derived from, a liquid part or a water extract of the first species and/or the second species. In some instances, the method includes wherein the endocide is an aqueous or organic extract or fraction thereof. In some instances, the method includes wherein the endocide is a dry or solubilized extract. In some instances, the method includes wherein the endocide is dry matter or derived from dry matter. In some instances, the method includes wherein the dry matter is ground or processed. In some instances, the method includes wherein the endocide is fresh matter or derived from fresh matter. In some instances, the method includes wherein the fresh matter is whole, chopped, or blended. In some instances, the method includes wherein the endocide is an extract or fraction expressed from the chopped or blended fresh matter. In some instances, the method includes wherein the endocide is decomposed matter or derived from decomposed matter. In some instances, the method includes wherein the endocide is a derivative and/or an analogue of a naturally occurring endocide. In some instances, the method includes wherein the endocide is a synthetic compound that is equivalent to a naturally occurring endocide.

In some instances, the method includes contacting the plant, propagule, or other propagative tissue with at least two endocides, derivatives thereof, and/or analogues thereof. In some instances, the method further includes contacting the plant, propagule, or other propagative tissue with a secondary agent.

The amounts of the ingredients within the compositions disclosed herein can vary (e.g., amounts can be as low as 0.000001% to as high as 98% w/w or any range therein). In some instances, the method includes wherein the composition comprises the endocide at concentration of 0.5-10% v/v. In some instances, the method includes wherein the plant, propagule, or other propagative tissue is contacted at room temperature.

The propagule or other propagative tissue can be from any plant. In some instances, the method includes wherein the propagule or other propagative tissue is from a woody plant or herbaceous plant. In some instances, the method includes wherein the propagule or other propagative tissue is from *C. acuminata, C. lowreyana, T. sebifera, M. alba, L. styraciflua, Q. texana, Q. shumardii, Q. michauxii, P. persica, I. vomitoria, E. pungens, O. ficus-indica, B. oleracea, A. hypogaea, S. canadensis*, and/or *S. molesta.*

In some instances, the method further includes enhancing biosynthesis and/or internal transport of at least one endocide in the propagule or other propagative tissue. In some instances, the method further includes soaking the propagule or other propagative tissue in water for at least 7 days, 10 days, 2 weeks, 4 weeks, 6 weeks, 8 weeks, 10 weeks, or 12 weeks.

In another aspect, there is disclosed a method of producing a mutation in a plant, the method comprising soaking a propagule or other propagative tissue in water for any amount of time. In some instances, the method includes soaking a propagule or other propagative tissue in water for at least 7 days, 10 days, 2 weeks, 4 weeks, 6 weeks, 8 weeks, 10 weeks, or 12 weeks.

The mutations induced by the methods and compositions disclosed herein can include any mutation. In some instances, the method includes wherein the mutation produced causes shrubbiness, dwarfism, pleiocotyly, abnormal leaf morphogenesis, small leaves, disturbed phyllotaxis or fasciated stems, variegation, modification in chemical biosynthesis, and/or derivatization of a chemical naturally found in a non-mutated plant of the species of the plant to be mutated. In some instances, the method includes wherein the mutation is found in the whole plant and/or at least one part of the plant. In some instances, the method includes wherein the propagule or other propagative tissue is contacted at room temperature.

The propagule or other propagative tissue can be from any plant. In some instances, the method includes wherein the propagule or other propagative tissue is from a woody plant or herbaceous plant. In some instances, the method includes wherein the propagule or other propagative tissue is from *C. acuminata, C. lowreyana, T. sebifera, M. alba, L. styraciflua, Q. texana, Q. shumardii, Q. michauxii, P. persica, I. vomitoria, E. pungens, O. ficus-indica, B. oleracea, A. hypogaea, S. canadensis*, and/or *S. molesta.*

In some instances, the method further includes contacting the propagule or other propagative tissue with at least one endocide to the species of the plant to be mutated, a derivative thereof, and/or an analogue thereof, wherein the endocide, derivative thereof, and/or analogue thereof is derived from the species of the plant to be mutated and/or a second closely related species. In some instances, the method further includes contacting the propagule or other propagative tissue with a secondary agent. In some instances, the method further includes enhancing biosynthesis and/or internal transport of at least one endocide in the propagule or other propagative tissue.

In yet another aspect, there is disclosed a method of producing a mutation in a plant, the method comprising enhancing biosynthesis and/or internal transport of at least one endocide in the plant. In some instances, the method includes wherein the method comprises pruning the plant. In some instances, the method includes wherein the method comprises fragmenting the plant. In some instances, the method includes removal of a majority of tissues from a propagule of the plant. In some instances, the method includes wherein the method comprises removal of a main above-ground plant stem of the plant. In some instances, the method includes wherein the method comprises removal of a main above-ground plant stem of the plant at 0-30 cm height. In some instances, the method includes wherein the method comprises removal of a main above-ground plant stem of the plant at 0-30 cm height in winter and/or when the plant is in dormancy.

In some instances, the method includes wherein the mutation produced causes shrubbiness, dwarfism, pleiocotyly, abnormal leaf morphogenesis, small leaves, disturbed phyllotaxis or fasciated stems, variegation, modification in chemical biosynthesis, and/or derivatization of a chemical naturally found in a non-mutated plant of the same species as the mutated plant. In some instances, the method includes wherein the mutation is found in the whole plant and/or at least one part of the plant.

The plant to be mutated can be any plant. In some instances, the method includes wherein the plant is a woody plant or herbaceous plant. In some instances, the method includes wherein the plant is *C. acuminata, C. lowreyana, T. sebifera, M. alba, L. styraciflua, Q. texana, Q. shumardii, Q. michauxii, P. persica, I. vomitoria, E. pungens, O. ficus-indica, B. oleracea, A. hypogaea, S. canadensis*, and/or *S. molesta*.

In some instances, the method further includes contacting a propagule or other propagative tissue of the plant with at least one endocide to the species of the plant to be mutated, a derivative thereof, and/or an analogue thereof, wherein the endocide, derivative thereof, and/or analogue thereof is derived from the species of the plant to be mutated and/or a closely related species. In some instances, the method further includes contacting the propagule or other propagative tissue of the plant with a secondary agent. In some instances, the method further includes soaking the propagule or other propagative tissue of the plant in water for at least 7 days, 10 days, 2 weeks, 4 weeks, or 6 weeks.

In one aspect, there is disclosed a method of producing a compound in a plant not produced in wildtype plants of the species of plant, comprising inducing a mutation in the plant according to any one of the methods disclosed herein. In some instances, the method includes identifying the compound. In some instances, the method further includes isolating the compound.

In another aspect, there is disclosed a method of producing and/or identifying a compound capable of inducing mutations in a plant and/or a mammalian subject, comprising identifying at least one compound from a mutated plant and/or mutated plant part mutated by any one of the methods disclosed herein, wherein the compound identified induces a mutation in a wildtype plant of the species the mutated plant and/or mutated plant part was derived. In some instances, the method includes wherein the identifying at least one compound from a mutated plant and/or mutated plant part comprises identifying at least one compound that is increased in concentration in the mutated plant and/or mutated plant part in comparison to a wildtype plant of the species the mutated plant was derived. In some instances, the method further includes testing the at least one compound for a capability of inducing mutations in a mammalian subject.

In yet another aspect, there is disclosed a chimera plant or a plant of a new variety and/or cultivar produced by any one of the methods disclosed herein. In some instances, the plant is propagated by an asexual and/or vegetative propagation method. In some instances, the plant is propagated by cuttings, striking, layering, division, budding grafting, stolons, runners, storage organs, twin-scaling, offsets, and/or micropropagation. In some instances, the plant is propagated by tissue or cell culture method. In some instances, the plant is propagated without application of a plant hormone. In some instances, the plant is propagated by genetic engineering, recombinant DNA technology, and/or genetic modification.

In one aspect, there is disclosed a new compound not previously known, produced by any one of the methods disclosed herein.

In another aspect, there is disclosed a product made at least in part of a whole plant or part of a plant of a new variety and/or cultivar produced by any one of the methods disclosed herein.

In some embodiments, the producing organisms are plants. In some embodiments, the producing organisms are woody plants. In some embodiments, the producing organisms are herbaceous plants. In some embodiments, the producing organisms are other groups of organisms.

In some embodiments, the induced mutations involve a whole plant or occur at the plant level. In some embodiments, the induced mutations are shrubbiness or dwarfism. In some embodiments, the induced mutations involve or are found only in part of a plant, such as at the tissue or organ level to produce a plant chimera. In some embodiments, the induced mutations are pleiocotyly (multicotyledonous). In some embodiments, the induced mutations are abnormal leaf morphogenesis, such as, but not limited to leaf teeth, lobe, bifid, or trifid development. In some embodiments, the induced mutations are disturbed phyllotaxis or fasciated stems. In some embodiments, the induced mutations are small leaves. In some embodiments, the induced mutations are variegation in leaves and/or stems. In some embodiments, the induced mutations are enlarged persistent leaves that are normally minute and are shed early.

Any measure of enhanced biosynthesis, internal transport, and/or external application of an endocide to the producing species or its closely related species is contemplated. In some embodiments, herein provided are methods of using pruning, especially decapitation of plants to enhance biosynthesis and/or internal transport of endocides and thus to induce mutations in plants, including total or partial mutations (chimeras). In some embodiments, provided are methods of using prolonged soaking of propagules in water to enhance biosynthesis or internal transport of endocides and thus to induce mutations in plants, including total or partial mutations (chimeras). In some embodiments, provided are methods of using external applications of endocides to treat propagules to induce mutations in plants, including total or partial mutations (chimeras).

In some embodiments, the treatment propagules are seeds. In some embodiments, the treatment propagules are fruits. In some embodiments, the treatment propagules are other plant organs or tissues.

An endocide (endogenous biocide) is a biocide derived from an endogenous bioactive agent (e.g., a secondary metabolite) that does not cause apparent poison in normal growth of the producing species but will poison or inhibit and even eliminate the parent species when induced to sufficient concentrations higher than that found during normal growth or when applied to the producing species and closely related species. Herein is disclosed that application of endocides will induce mutations in the parent species and its closely-related species. In some instances, the mutagenic properties of an endocide is selective for the species in which it is found and/or closely related species. In some instances, an endocide is selective for the species in which it is found and/or a closely related species. Herein is also disclosed that 4-hydroxybenzoic acid and 3,4-dihydroxybenzoic acid are endocides derived from *Salvinia molesta*. Also disclosed herein is that derivatives and/or analogs of 4-hydroxybenzoic acid and 3,4-dihydroxybenzoic acid retain the endocidal activity of the parent compound.

In some embodiments, the endocide is an extract from the species that the growth is to be modified or a closely-related species. In some embodiments, the endocide is a fraction of extract from the producing or closely-related species to be developed. In some embodiments, the endocide is a compound isolated from the producing or closely-related species to be developed. In some embodiments, the endocide is dry matter from the producing or closely-related species to be developed. In some embodiments, the endocide is fresh matter from the producing or closely-related species to be developed. The endocide "derived from a species" may be any composition or compound originally obtained from a species, even if further modified. It also encompasses synthetic compounds that are equivalent to the compounds derived from the species or derivatives thereof.

In some embodiments, provided are methods of inducing mutations in a species comprising applying a composition comprising an endocide, wherein the endocide is derived from the organism or its closely-related species. Any measure of making endocide effective to the target species is contemplated. In some embodiments, the effective pruning, especially decapitation involves removal of main plant stem from above ground at 0-30 cm height in winter. In some embodiments, the effective prolonged soaking of propagules in water involves soaking at room temperature for 4-12 weeks. In some embodiments, the effective soaking of propagules in an endocide involves soaking in an endocide containing extract of the species of plant to be mutated at concentration of 0.5-10% v/v at room temperature for 24 h to 12 weeks.

In some embodiments, induced mutations in plants, including total or partial mutations (chimeras) by application of endocides can be used to develop desirable new variety or cultivar by any propagation method. In some embodiments, the propagation is an asexual or vegetative propagation method, including cuttings or striking, layering, division, budding grafting, stolons or runners, storage organs (e.g., bulbs, corms, tubes, and rhizomes), twin-scaling, offsets, and micropropagation. In some embodiments, the micropropagation method is tissue or cell culture method. In some embodiments, the asexual or vegetative propagation is used without application of any plant hormone.

In some embodiments, the propagation is a sexual propagation method, e.g., by seeds or fruits through sowing.

In some embodiments, the propagation method used is by genetic engineering, recombinant DNA technology, or genetic modification. In some embodiments, such a technology is the transfer of specific traits or genes from the mutated species induced by endocide into other organisms.

In some embodiments, the new variety or cultivar can be used as a crop in agriculture. In some embodiments, the agricultural crop is for production of food. In some embodiments, the agricultural crop is for production of pulses. In some embodiments, the agricultural crop is for production of food adjuncts. In some embodiments, the agricultural crop is for production of vegetables. In some embodiments, the agricultural crop is for production of fruits. In some embodiments, the agricultural crop is for production of nuts. In some embodiments, the agricultural crop is for production of oilseeds. In some embodiments, the agricultural crop is for production of spices or condiments. In some embodiments, the agricultural crop is for production of green and green leaf manure.

In some embodiments, the agricultural crop is for production of livestock fodder. In some embodiments, the agricultural crop is for production of biomass. In some embodiments, the agricultural crop is for production of other agricultural products.

In some embodiments, the new variety or cultivar can be used as a timber crop in forestry. In some embodiments, the new variety or cultivar can be used as a pulpwood crop in forestry. In some embodiments, the new variety or cultivar can be used as other crop in forestry.

In some embodiments, the new variety or cultivar can be used as ornamental or landscape uses in horticulture.

In some embodiments, the new variety or cultivar can be used as an industrial crop. In some embodiments, the industrial crop is for production of fibers. In some embodiments, the industrial crop is for production of beverages. In some embodiments, the industrial crop is for production of narcotics. In some embodiments, the industrial crop is for production of rubber. In some embodiments, the industrial crop is for production of sugars and starches. In some embodiments, the industrial crop is used for production of a biofuel. In some embodiments, the biofuel is alcohol. In some embodiments, the biofuel is diesel. In some embodiments, the industrial crop is used for production of specialty chemicals.

In some embodiments, the new variety or cultivar can be used as a pharmaceutical crop. In some embodiments, the new variety or cultivar can be used as a medicinal plant.

In some embodiments, provided are methods of induced mutations are not only in form of phenotypic changes but also in increase of chemical biosynthesis and derivatization. Any above described methods in this invention can induce production of minor or new compounds that did not occur in the species and/or nature previously. This method can be used to identify and isolate new bioactive compounds.

In some aspects, the concentration of an endocide determines if a mutation is induced or if the endocide kills the organism or living tissues.

In some aspects, disclosed herein is a method of controlling an unwanted species comprising applying a composition comprising an endocide to the species, a derivative thereof, and/or an analogue thereof. In some instances, the endocide, derivative thereof, and/or analogue thereof is 4-hydroxybenzoic acid, 3,4-dihydroxybenzoic acid, benzoic acid, 2-hydroxybenzoic acid, 3-hydroxybenzoic acid, 2,3-dihydroxybenzoic acid, 2,4-dihydroxybenzoic acid, 2,5-dihydroxybenzoic acid, 2,6-dihydroxybenzoic acid, 3,5-dihydroxybenzoic acid, 2,3,4-trihydroxybenzoic acid, 2,4,6-trihydroxybenzoic acid, 3,4,5-trihydroxybenzoic acid, phenoxyacetic acid, isonicotinic acid, and/or nicotinic acid. In some instances, the species to be controlled is in the order of Salviniales. In some instances, the species is *Salvinia molesta* and/or *Azolla caroliniana*. In some instances, the species is resistant to a pesticide, herbicide, drug, or chemical treatment used to control the species. In some instances, the growth, reproduction, or spread is halted. In some instances, the species is eliminated. In some instances, the growth, reproduction, or spread is halted within 1 week or 1 month. In some instances, the growth, reproduction, or spread is halted for at least 1 year. In some instances, the composition comprising the endocide, derivative thereof, and/or analogue thereof is applied topically to, applied to a trichome of, sprayed on, spread around, and/or dissolved in water surrounding the species. In some instances, the composition contains about 0.01% or more, 0.015%, 0.031%, 0.063%, 0.1% 0.125%, 0.25%, 0.5%, 1%, 2%, 4%, 6%, 10% or more by weight of the endocide, derivative thereof, and/or analogue thereof.

In some aspects, disclosed herein is a composition for modifying the growth of a species comprising an endocide to the species, a derivative thereof, and/or an analogue thereof. In some instances, the endocide, derivative thereof, and/or analogue thereof is 4-hydroxybenzoic acid, 3,4-dihydroxybenzoic acid, benzoic acid, 2-hydroxybenzoic acid, 3-hydroxybenzoic acid, 2,3-dihydroxybenzoic acid, 2,4-dihydroxybenzoic acid, 2,5-dihydroxybenzoic acid, 2,6-dihydroxybenzoic acid, 3,5-dihydroxybenzoic acid, 2,3,4-trihydroxybenzoic acid, 2,4,6-trihydroxybenzoic acid, 3,4,5-trihydroxybenzoic acid, phenoxyacetic acid, isonicotinic acid, and/or nicotinic acid. In some instances, the species to be controlled is in the order of Salviniales. In some instances, the species is *Salvinia molesta* and/or *Azolla caroliniana*. In some instances, the composition contains about 0.01% or more, 0.015%, 0.031%, 0.063%, 0.1% 0.125%, 0.25%, 0.5%, 1%, 2%, 4%, 6%, 10% or more by weight of the endocide, derivative thereof, and/or analogue thereof.

In some embodiments, the endocide may be applied alone. In some embodiments, the endocide may be applied in combination with one or more secondary agents. In some embodiments, the secondary agent may be an endocide from closely related species or another species. In some embodiments, the secondary agent may be a mutagen, formic acid, acetic acid, diquat (diquat dibromide), soap, glyphosate, contact herbicides and/or other types of biocides and/or biocontrol agents. In some embodiments, the secondary agent is a preservative, an antioxidant, an adjuvant, a stabilizer, a binder, a surfactant, an emulsifier, an effervescent, a wetting agent, a carrier, a diluent, etc.

The efficacy and selectivity of the endocide can be improved or enhanced by combination of two or more endocides from the same and/or different species.

In some embodiments, the endocide is a compound modified from an endogenous bioactive agent and/or endogenous endocide, thus the endocide is a compound not found in the species wherein a non-modified endocide is naturally found and/or the endocide is not a naturally occurring compound. In some embodiments, the endocide is an analogue or derivative of a naturally occurring endogenous bioactive agent and/or endogenous endocide. In some embodiments, the endocide is 4-hydroxybenzoic acid. In some embodiments, the endocide is 3,4-dihydroxybenzoic acid. In some embodiments, the endocide is the combination of 4-hydroxybenzoic acid and 3,4-dihydroxybenzoic acid. In some embodiments, it is more effective to apply the endocide with one or more surfactants or adjuvants. In some embodiments, the surfactant is DAWN® dish soap. In some embodiments, the surfactant is DYNE-AMIC®.

In some aspects, mutations are induced in *S. molesta*. In some instances, new growth of type I will be induced after all leave tissues are killed by a sufficiently high level of endocides are induced and/or applied or killed by other factors (e.g., herbicides, weevils, freeze). Type I growth of *S. molesta* (previously known as "primary stage" or "primary growth stage") refers to the plants with the small, flat, and oval-shaped floating leaves less than 15 mm in width. For other factors, in some instances, the mutations are induced if the endocides are released by the dead tissues becomes available to the surviving buds. In some instances, if the endocides are not available to the surviving buds (e.g., example 13 showing the dead tissues removed away from the buds), there will be no type I mutation.

In some instances, new growth of type II will be induced when *Salvinia* plants are severely injured (e.g., fragmenting to remove most or all leaves from buds). Type II growth of *S. molesta* (previously known as "secondary stage" or "secondary growth stage") refers to the plants with the slightly cupped floating leaves ranging between 15 mm and 50 mm in width. In some instances, the injury increases production of endocides in the plant. In some instances, the some instances, the increased endocides will induce type II mutation. In some instances, the endocides are induced to a lower concentration than some external applications or that provided from dead tissues.

In some aspects, the level of externally applied endocides or available endocides from dead tissues is sufficiently high to kill all tissues and/or inhibit regrowth.

In some embodiments, the endocide may selectively modify growth and/or induce mutations in the species from which the endocide is derived over other species. In some embodiments, the endocide may selectively modify growth and/or induce mutations in a target species over other species. In some embodiments, the endocide may selectively modify growth and/or induce mutations in the species from which the endocide is derived and/or the species to be treated and its closely-related species over other species. In some embodiments, a closely-related species is a species within the same genus. In some embodiments, a closely-related species is a species within the same family. In some embodiments, a closely-related species is a species within the same order. In some embodiments, a closely-related species is a species within the same class. In some embodiments, selective activity for the species to be treated is over a species that is not in the genus, family, order, or class of the species to be treated.

The endocide may be present in any appropriate concentration in the composition. In some embodiments, the composition contains 0.00001, 0.0001, 0.001, 0.01, 0.1, 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% by weight or more of the endocide. In some embodiments, the composition contains about 0.00001 to about 20% by weight of the endocide. In some embodiments, the composition contains about 0.1 to 10% by weight of an extract containing at least one endocide.

Also disclosed are the compositions as described herein, as well as kits containing the same.

"Mutation" as described herein is a sudden departure from the parent type in one or more inheritable or non-inheritable characteristics. Development of an observable mutated characteristic is also known as abnormal morphogenesis. A mutation can be helpful, harmful, or neutral to the organism.

"Propagule" and "propagules" as described herein is any plant material that is capable of propagating a plant and/or giving rise to an individual organism. Non-limiting examples of propagules include seeds, fruits, sections, cuttings, spores, buds, stolons, runners, storage organs, etc.

"Shrubbiness" as described herein is any development of multiple stems directly from the same radicle and/or from the main stem. A non-limiting example of multiple stems developed directly from the same radicle include a suckering shrub. In some embodiments, shrubbiness can be used to describe a woody and/or a herbaceous plant species. Non-limiting examples include a shrub or shrub-like form of a tree, shrub-like habit of a herbaceous plant, a dwarf form of a woody plant, and/or a dwarf form of a herbaceous plant species.

"Salvinias" means aquatic or semi-aquatic fern species of the order Salviniales, including families Salviniaceae Reichenbach (*Salvinia* Séguier), Azollaceae Wettstein (*Azolla* Lamarck) (sometimes, *Azolla* is treated as a genus of the family Salviniaceae), and Marsileaceae Mirbel (*Marsdea* L., *Pilularia* L., and *Regnellidium* Lindm).

Type I of giant *salvinia* (*Salvinia molesta*) (previously known as "primary stage" or "primary growth stage") refers to the plants with the small, flat, and oval-shaped floating leaves less than 15 mm in width.

Type II of giant *salvinia* (*Salvinia molesta*) (previously known as "secondary stage" or "secondary growth stage") refers to the plants with the slightly cupped floating leaves ranging between 15 mm and 50 mm in width.

Type III of giant *salvinia* (*Salvinia molesta*) (previously known as "tertiary stage" or "tertiary growth stage") refers to the plant with tightly folded and large floating leaves that are more than 50 mm in width when forced open.

The term "invasive species" means a species (e.g., plants including fungi and animals including insects) that is either native or non-native (exotic) to the ecosystem and whose presence or introduction causes or likely causes economical or environmental harm or harm to human health.

"Invasive plant species" or "invasive plant" means either a non-native (exotic) or native invasive plant species.

"Invasive aquatic species" or "aquatic invasive species" means an invasive species that has living in, on, or next to water.

"Invasive aquatic plant" means an invasive plant species that has adapted to living in, on, or next to water, and that can grow either submerged or partially submerged in water.

"Unwanted species" means a species (e.g., plants, fungi, Protista, Monera, and animals including insects) that is not wanted or desired. It can be either native or non-native (exotic) to the ecosystem. In some embodiments, it is an invasive species. In some embodiments, it is a weed. In some embodiments, it is a nuisance species. In some embodiments, it is a noxious species. In some embodiments, it is a species that is unwanted in a particular location. The location can be, but is not limited to, a geographic region, a park or recreational area, a field for crops, a body of water, a garden, a landscaped yard, a flower bed, a building, and/or an area around such locations. In some embodiments, the species is not an invasive species. In some embodiments, the species presence or introduction does not cause or likely causes economical or environmental harm or harm to human health.

"Weed" means a plant considered undesirable in a particular situation.

"Water body" or "body of water" means any significant accumulation of water on a planet's surface, including but not limited to a lake, pond, river, canal, creek, stream, brook, channel, ditch, bay, bayou, swamp, marsh, slough, bog, fen, wetland, harbor, inlet, lagoon, puddle, reservoir, strait, spring, swimming pool, or any container or structure with permanent or seasonal water.

"Gland" means a cell, group of cells, or organ producing a secretion. "Exocrine gland" means any gland that secretes its products through a duct onto an epithelial surface.

"Trichome" refers to "glandular trichome" or plant gland in this invention and means glandular unicellular or multi-cellular appendages on the surface of various plant organs.

"Effective" amount or concentration means that amount or concentration which, when applied to a place or subject for controlling an invasive or unwanted species, is sufficient to induce a mutation, and/or is sufficient to affect the growth, reproduction, or spread of the species.

"Control" or "controlling" means one or all of the following three actions or processes: elimination or eliminating, inhibition or inhibiting, and/or prevention or preventing. (1) "Elimination" or "eliminating" refers to eradicating, killing, or destroying completely one or all propagules or whole individuals of an invasive or unwanted species in a place or subject. (2) "Inhibition" or "inhibiting" refers to slowing, interrupting, or arresting growth, reproduction, or spread of an invasive or unwanted species in a place or subject. As used herein, the term "inhibition" or "inhibiting" does not necessarily indicate a total elimination of the species. (3) "Prevention" or "preventing" refers to the action or process of stopping growth, reproduction, or spread of an invasive or unwanted species in a place or subject or keeping an invasive or unwanted species from happening in a place or subject.

"Decapitation pruning" means pruning of apical shoots and/or topping at the onset of flowering, also known as "T-pruning," of a target plant.

"Fragmenting" means a process of breaking a plant or tissue into small or separate parts (fragments).

"Modify growth" or "modifying growth" means one or all of the following control, controlling, mutate, mutating, change, changing, eliminate, eliminating, inhibit, inhibiting, prevention, or preventing the growth of an organism, a part of an organism, or a group of organisms.

"Analogue" and "analog," when referring to a compound, refers to a modified compound wherein one or more atoms have been substituted by other atoms, or wherein one or more atoms have been deleted from the compound, or wherein one or more atoms have been added to the compound, or any combination of such modifications. Such addition, deletion or substitution of atoms can take place at any point, or multiple points, along the primary structure comprising the compound.

"Derivative," in relation to a parent compound, refers to a chemically modified parent compound or an analogue thereof, wherein at least one substituent is not present in the parent compound or an analogue thereof. One such non-limiting example is a parent compound which has been covalently modified. Typical modifications are amides, carbohydrates, alkyl groups, acyl groups, esters, pegylations and the like.

"Subject" refers to a mammal (e.g., human, primate, dog, cat, bovine, ovine, porcine, equine, mouse, rate, hamster, rabbit, or guinea pig). In particular aspects, the subject is a human.

Some abbreviations used herein are as follows: CH₃CN is acetonitrile, cm is centimeter(s), CPT is camptothecin, EtOH is ethanol, g is gram(s), h is hour(s), H₂O is water, HPLC is high performance liquid chromatography, kg is kilogram(s), L is liter(s), m is meter(s), mg is milligram(s), min. is minute(s), mL is milliliter(s), mm is millimeter(s), psi is pounds per square inch, s is second(s), and µM is micrometer(s).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A-6D—Seedlings of *Arachis hypogaea* germinated from the seeds soaked in 5% EtOH extracts of *A. hypogaea* peanut shell for one week developed abnormal leaf morphogenesis (B-D) in comparison with normal seedlings germinated from the seeds without any treatment (A).

FIG. 7—Induced pleiocotyly in *Triadica sebifera* by the prolonged seed soaking in water for six weeks. The photos show the normal cotyledon development (middle plant), cotyledon with two lobes (two fused cotyledons) (left), and tricotyledon (right).

DESCRIPTION OF ILLUSTRATIVE EMBODIMENTS

Figure 1:
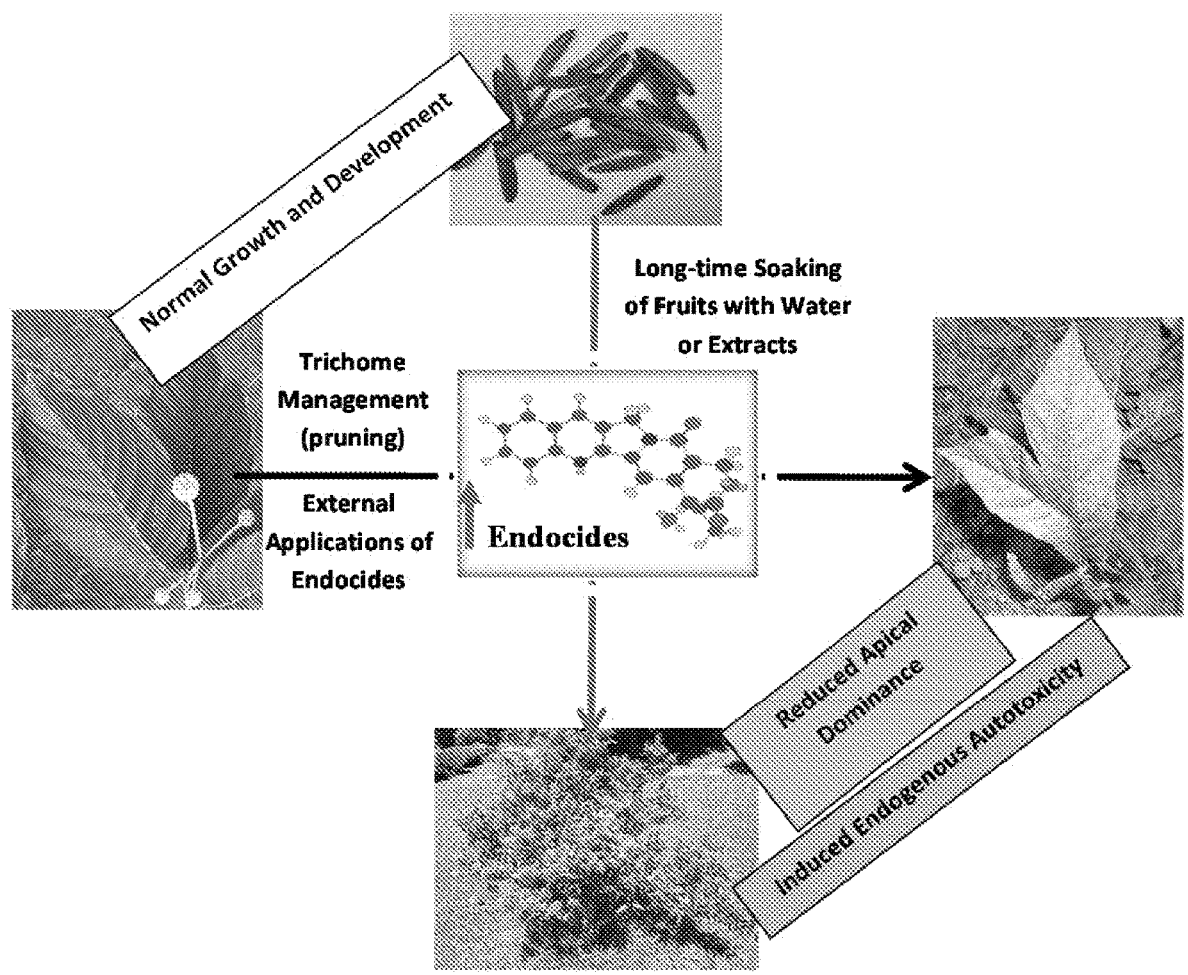
FIG. 1—The diagram shows the enhanced production of endocidal camptothecins (CPTs) by "Trichome Management" techniques (e.g., decapitation pruning) or external applications of CPTs in *Camptotheca* trees. This abnormal morphogenesis can also be induced through extended periods of soaking the fruits in water or *Camptotheca* extracts. These endocide inductions or applications directly reduced apical dominance of *Camptotheca*, resulting in shrubbiness in *Camptotheca* tree.
Figure 2:
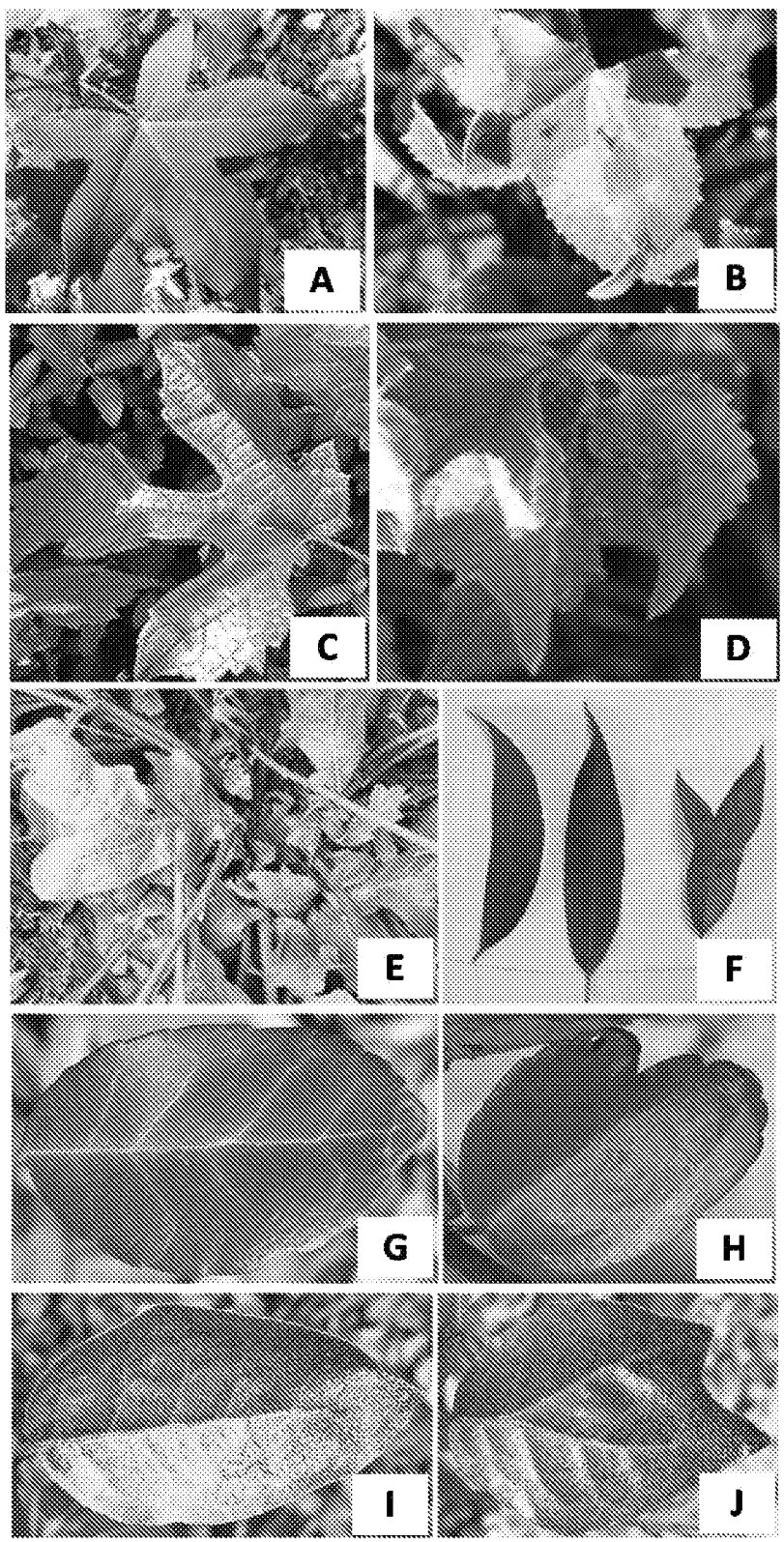
FIG. 2A-2J—Lobed leaves developed in April in *Liquidambar styraciflua* (A. normal; B. abnormal), *Morus alba* (C. normal; D. abnormal), E. *Quercus shumardii*, F. *Prunus persica*, *Ilex vomitoria* (G. normal; H. abnormal), *Elaeagnus pungens* (I. normal; J. abnormal) following decapitation pruning in the previous December.

As disclosed herein, specific pruning of plants, prolonged water soaking of propagules, and extracts soaking of propagules can induce mutations. Mutations in plants may include mutations found in the entire plant or part of the plant (chimeras).

Further, in newly-developed tissues in the treated plants or young seedlings developed from the treated fruits or seeds, chemical diversity of secondary metabolites are significantly enhanced. As disclosed herein, decapitation pruning of *C. acuminata* trees significantly induced biosynthesis of some new compounds not occurring naturally in the species. From the abnormal *Q. shumardii* seedlings germinated from the acorns treated by its acorn extracts (Example 5), a unique compound was found that was not detected in either acorns or normal seedlings (Example 8). This unique compound is a metabolic product of the abnormal oak seedlings.

Providing some endocides at higher dosage can kill, inhibit growth, and inhibit germination or reduce germination capacity of plants; however, the endocides at lower dosage will cause mutations in plants and allow some seeds to germinate but induce mutations in germinated seedlings.

1. Mutation by Pruning

As disclosed herein, specific pruning causes mutations in plants and/or new species. Such mutations and/or variations include, but are not limited to, development of coppiced plant with multiple stems (suckering) and development of leaf teeth. To date, there is no reported pruning technology suggested to develop a new plant variety, or pruning that causes mutations correlated with increased endogenous concentrations of endocides that are species specific and/or species and closely related species specific.

Herein is disclosed that mutations can be induced by pruning or fragmenting.

TABLE 1

Woody species list in the decapitation pruning or fragmenting experiments

| Kingdom | Phyllum/Division | Family | Species | Common Name | Status in North America |
|---|---|---|---|---|---|
| Plantae | dicots of Anthophyta (angiosperms) | Nyssaceae | *Camptotheca acuminata* Decaisne | happytree | cultivated |
| Plantae | dicots of Anthophyta (angiosperms) | Nyssaceae | *C. lowreyana* Li | Lowrey's happytree | cultivated |
| Plantae | dicots of Anthophyta (angiosperms) | Euphorbiaceae | *Triadica sebifera* (L.) Small | Chinese tallow | invasive |
| Plantae | dicots of Anthophyta (angiosperms) | Moraceae | *Morus alba* L. | mulberry | native & unwanted |
| Plantae | dicots of Anthophyta (angiosperms) | Altingiaceae | *Liquidambar styraciflua* L. | sweetgum | native & unwanted |
| Plantae | dicots of Anthophyta (angiosperms) | Fagaceae | *Q. shumardii* Buckley | Shumard oak | native |
| Plantae | dicots of Anthophyta (angiosperms) | Rosaceae | *Prunus persica* (L.) Stoles | peach tree | cultivated |
| Plantae | dicots of Anthophyta (angiosperms) | Aquifoliaceae | *Ilex vomitoria* Sol. Ex Alton | yaupon | native |
| Plantae | dicots of Anthophyta (angiosperms) | Elaeagnaceae | *Elaeagnus pungens* Thunb. | thorny olive | invasive |
| Plantae | dicots of Anthophyta (angiosperms) | Adoxaceae | *Sambucus Canadensis* L. | elderberry | native |
| Plantae | Pteridophyta | Salviniaceae | *S. molesta* D. S. Mitchell | Giant salvinia | invasive |

As disclosed herein, chimeras with abnormal morphogenesis were observed following decapitation pruning in *C. acuminata, C. lowreyana, T. sebifera, M. alba, L. styraciflua, Q. texana, Q. shumardii, Q. michauxii, P. persica, I. vomitoria, E. pungens, O. ficus-indica, B. oleracea, A. hypogaea, S. canadensis,* and/or *S. molesta*.

It is expected that the method disclosed herein is capable of inducing mutations in a broad range of species. Further, it is expected that in some instances, an endocide induced in a plant by the methods is capable of inducing mutations in a broad range of species, in mammals, and/or in humans. It is also expected that in some instances, an endocide induced by the method is capable of inducing mutations only in the species from which the chimera was derived or also in closely related species.

2. Mutation by Soaking

In current agricultural, forestry, and horticultural practices, short seed soaking in water (usually <24 h, occasionally up to several days) is recommended and prolonged soaking in water for several weeks is always avoided for optimal germination. By contrast, the inventor determined that prolonged soaking of seeds or fruits in water (several weeks) induces mutations in plants, including total mutations or partial mutations (chimeras). The mutations include, but are not limited to abnormal leaf morphogenesis in germinated seedlings similar to those induced by pruning, shrubbiness or dwarf habit, and abnormally large number of cotyledons (known as pleiocotyly or polycotyly) and/or cotyledon with two lobes (may also be interpreted as two fused cotyledons).

Herein is disclosed that unconventional prolonged soaking of fruits or seeds of woody and herbaceous plants (Table 2) in water will induce mutations.

TABLE 2

Experimental species list for unconventional prolonged soaking experiments

| Kingdom | Phyllum/Division | Family | Species | Common Name | Status in North America |
|---|---|---|---|---|---|
| Plantae | dicots of Anthophyta (angiosperms) | Nyssaceae | *Camptotheca acuminata* Decaisne | happytree | cultivated |
| Plantae | dicots of Anthophyta (angiosperms) | Nyssaceae | *C. lowreyana* Li | Lowrey's happytree | cultivated |
| Plantae | dicots of Anthophyta (angiosperms) | Nyssaceae | *C. lowreyana* Li 'Hicksii' | Hicks happytree | cultivated |

TABLE 2-continued

Experimental species list for unconventional prolonged soaking experiments

| Kingdom | Phyllum/ Division | Family | Species | Common Name | Status in North America |
|---|---|---|---|---|---|
| Plantae | dicots of Anthophyta (angiosperms) | Fagaceae | *Quercus shumardii* Buckley | Shumard oak | native |
| Plantae | dicots of Anthophyta (angiosperms) | Fagaceae | *Q. texana* Buckley | Nuttall oak | native |
| Plantae | dicots of Anthophyta (angiosperms) | Fagaceae | *Q. michauxii* Nuttall | swamp chestnut oak | native |
| Plantae | dicots of Anthophyta (angiosperms) | Fabaceae | *Arachis hypogaea* L | peanut | crop |
| Plantae | dicots of Anthophyta (angiosperms) | Euphorbiaceae | *Triadica sebifera* (L.) Small | Chinese tallow | invasive |
| Plantae | Pteridophyta | Salviniaceae | *S. molesta* D. S. Mitchell | Giant *salvinia* | invasive |

Non-limiting examples disclosed herein include induction of mutation in greenhouse experiments using *Camptotheca* spp. *Camptotheca* spp. usually has no branch development in the early seedling stage. However, following the fruits soaked in water for four weeks, 15.6% *C. acuminata* seedlings developed 2-3 branches and 38.5% seedlings of *C. lowreyana* had 2-5 branches from the main stem (Example 3).

Figure 5:
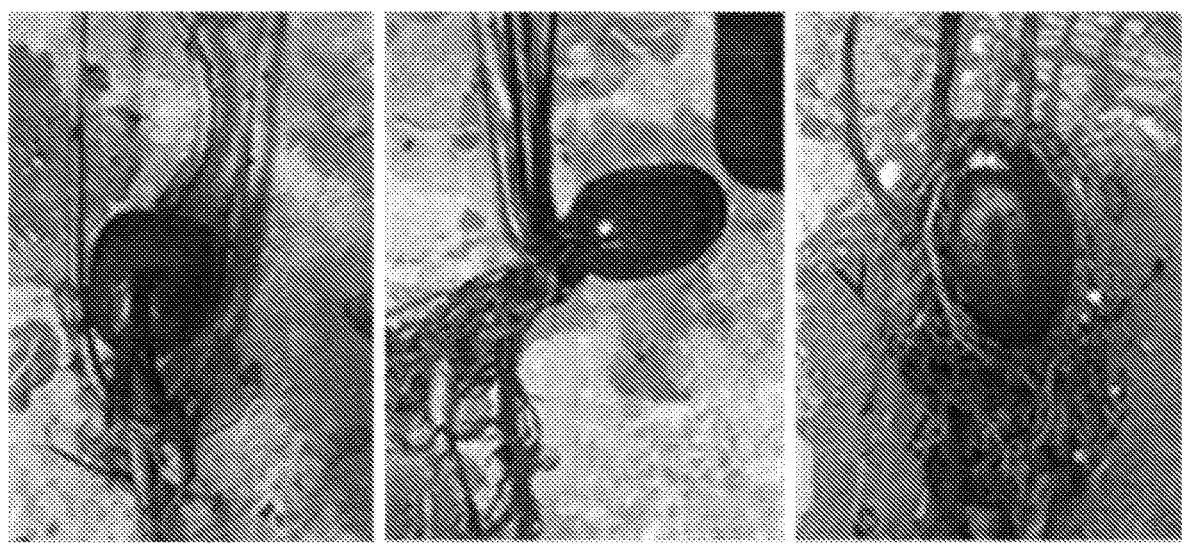
FIG. 5—7.32, 8.64, and 19.27% of the germinated acorns of *Quercus* shumardii (left), *Q. texana* (middle), or *Q. michauxii* (right) developed 2-3 stems, respectively, each after the bulk acorns soaked in relative small volume of water for about a month.

Similar to *Camptotheca*, *Quercus* acorn soaking also induced significant abnormal morphogenesis. A prolonged soaking of bulk acorns in just enough water to cover all acorns for four weeks induced significant multiple stem development in both red oaks (*Q. shumardii* and *Q. texana*) and white oaks (e.g., *Q. michauxii*) (FIG. 5). The results are very similar to the short-term (48 h) soaking in acorn extracts containing endocides. Acorn endocides released from long soaking or external applied causes reduced apical dominance or shrubbiness (development of multiple stems directly from the same radicle like a suckering shrub and/or from the main stem).

Figure 7:
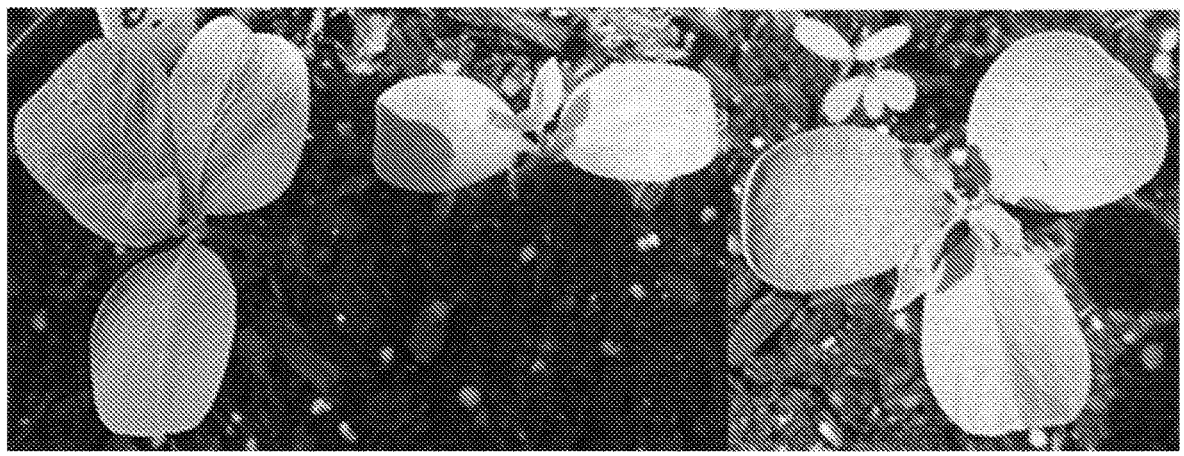

In another example, 10.6% of *T. sebifera* seedlings had pleiocotyly (3 or 4 cotyledons and cotyledons with two lobes) after the seeds were soaked in water for six weeks (FIG. 7 left and right figures compared to normal growth in middle figure).

Soaking of *S. molesta* in water with air-dried whole plants of *S. molesta* is known to kill the plants (U.S. application Ser. No. 14/889,184, example 1). Herein is disclosed that prolonged soaking of dense *S. molesta* in limited volume of water killed some plants and induced some remaining tissues of *S. molesta* to develop mutations. Not to be bound by theory, it is believed that release of endocides damaged and killed some tissues and that dead and/or damaged tissues further released endocides, increasing the concentrations of endocides in the water. The concentrations of endocides killed some plants and induce some remaining tissues of *S. molesta* to develop mutations. Similar to *Camptotheca* (e.g., cultivar 'Katie' and 'CT168' with small leaves), the induced mutations in any type of *S. molesta* plants include multiple branches with small floating leaves. These mutations can occur after the death of all floating leaves. Similar forms of small leaves have been commonly believed to be the early growth stage of *S. molesta* known as the "primary stage" (vs. slightly cupped medium size floating leaves known as the "secondary stage" and larger and tightly folded floating leaves known as the "tertiary stage"). However, it is disclosed herein that the type of new growth in *S. molesta* primarily depends on the plant "growth stage" and the conditions under which the disturbance occurs. With no or with slight disturbance, a *S. molesta* plant at the "tertiary stage" develops a "tertiary" new growth, a plant at the "secondary stage" produces "secondary" new growth, and a plant at the "primary stage" has "primary" new growth only. Not to be bound by theory, after apical cuttings, it is believed that fragmenting (e.g., removing buds with or without leaves from *S. molesta* plants) enhance the endocide level and plants develop "secondary" or "primary" new growths. Also, if all floating leaves are killed, it is believed that endocides released by the dead tissues induces "primary" new growth from plants of any stage. Further, it is disclosed herein that some "primary" *S. molesta* plants remained in the "primary" stage until their death. Thus, the known "growth stages" of *S. molesta* are not heteroblastic development between juvenile and adulthood. Herein we name these "growth stages" as growth types: "primary stage" as type I, "secondary stage" as type II, and "tertiary stage" as type III.

The type I *S. molesta* was induced by high level of endocides after all floating leaves were killed, the type II *S. molesta* was induced by moderate level of endocides after the plant was severely damaged, and type III form of new growth was produced from large plants (type III) with no or slight disturbance.

In some embodiments, type II new growth was developed from fragmented buds (from type III *S. molesta* plants) with a few leaves (e.g. couple of pairs) or buds with a few floating leaves (e.g. couple of pairs) remained after endocide treatments (Examples 12 and 13). The experiments also show that culture of buds (physically removed from leaves) alone will lead to the development of type I growth (Example 13). Thus, not to be bound by theory, remaining living tissues may need to be poisoned by endocides to induce type I development. The endocides may be from the enhanced production in the surviving propagules following damages, dead tissues of the plants, or from external application.

Some induced type I *S. molesta* plants might remain small in size until their death. In some embodiments, type I plants might grow into type II and even type III when the concentration of endocides decreases over time.

It is expected that the method disclosed herein is capable of inducing mutations in a broad range of species. Further, it is expected that in some instances, an endocide induced in a plant by the methods is capable of inducing mutations in a broad range of species, in mammals, and/or in humans. It is also expected that in some instances, an endocide induced by the method is capable of inducing mutations only in the species from which the plant was derived or also in closely related species.

3. Mutation by Application with Endocides

It is also disclosed herein that external applications of endocides to treat seeds, fruits, or other part of reproductive organs or tissues to induce mutations in plants, including total or partial mutations (chimeras). In some embodiments, the induced mutations includes mutations in the whole plant or at least one part of the plant. In some embodiments, soaking the fruits, seeds, or vegetative parts of woody and herbaceous plants (Table 3) with endocides will induce mutations.

TABLE 3

Experimental species list for soaking experiments with endocides

| Kingdom | Phyllum/Division | Family | Species | Common Name | Status in North America |
|---|---|---|---|---|---|
| Plantae | dicots of Anthophyta (angiosperms) | Fabaceae | *Arachis hypogaea* L | peanut | crop |
| Plantae | dicots of Anthophyta (angiosperms) | Euphorbiaceae | *Triadica sebifera* (L.) Small | Chinese tallow | invasive |
| Plantae | dicots of Anthophyta (angiosperms) | Fagaceae | *Q. shumardii* Buckley | Shumard oak | native |
| Plantae | dicots of Anthophyta (angiosperms) | Brassicaceae | *Brassica oleracea* L. | broccoli | crop |
| Plantae | dicots of Anthophyta (angiosperms) | Cactaceae | *Opuntia ficus-indica* (L.) Mill. | nopal cactus or Indian fig opuntia | crop |

Figure 6:
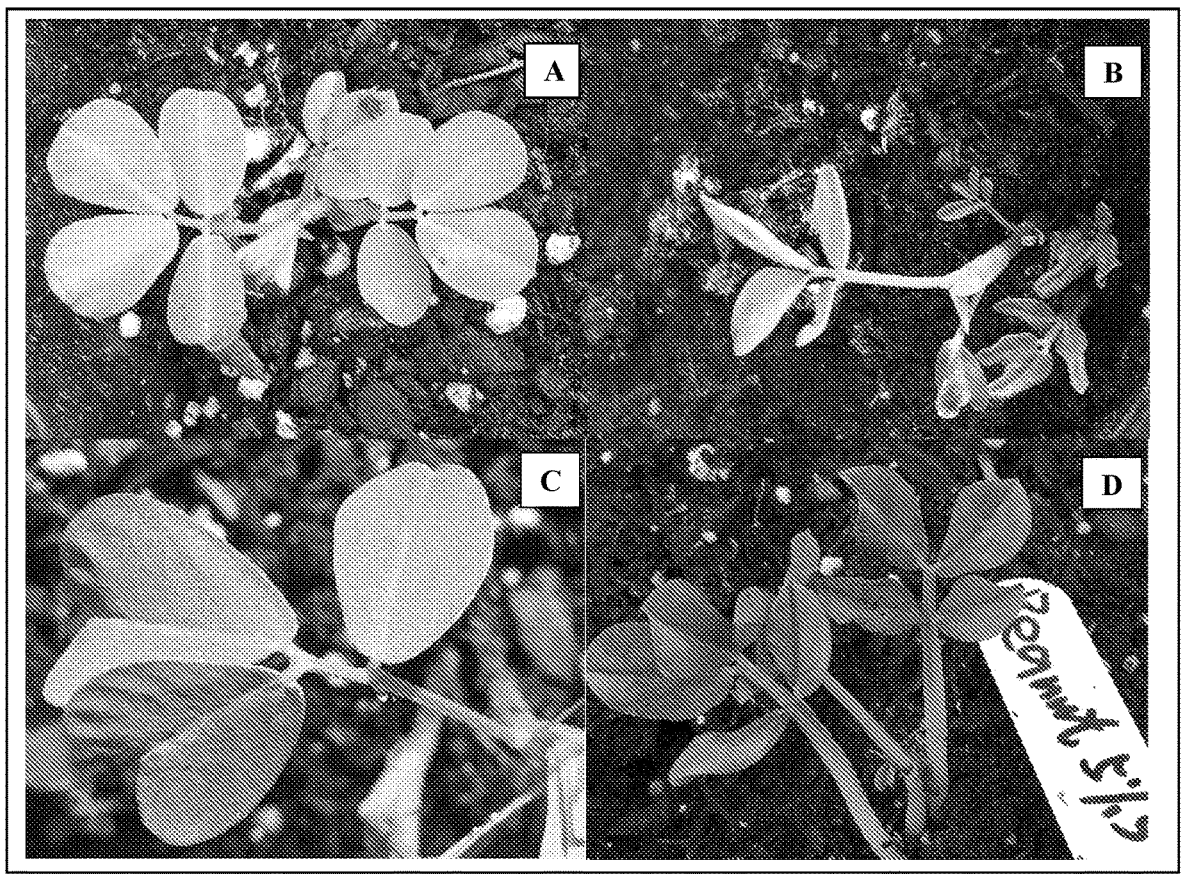
Figure 8:
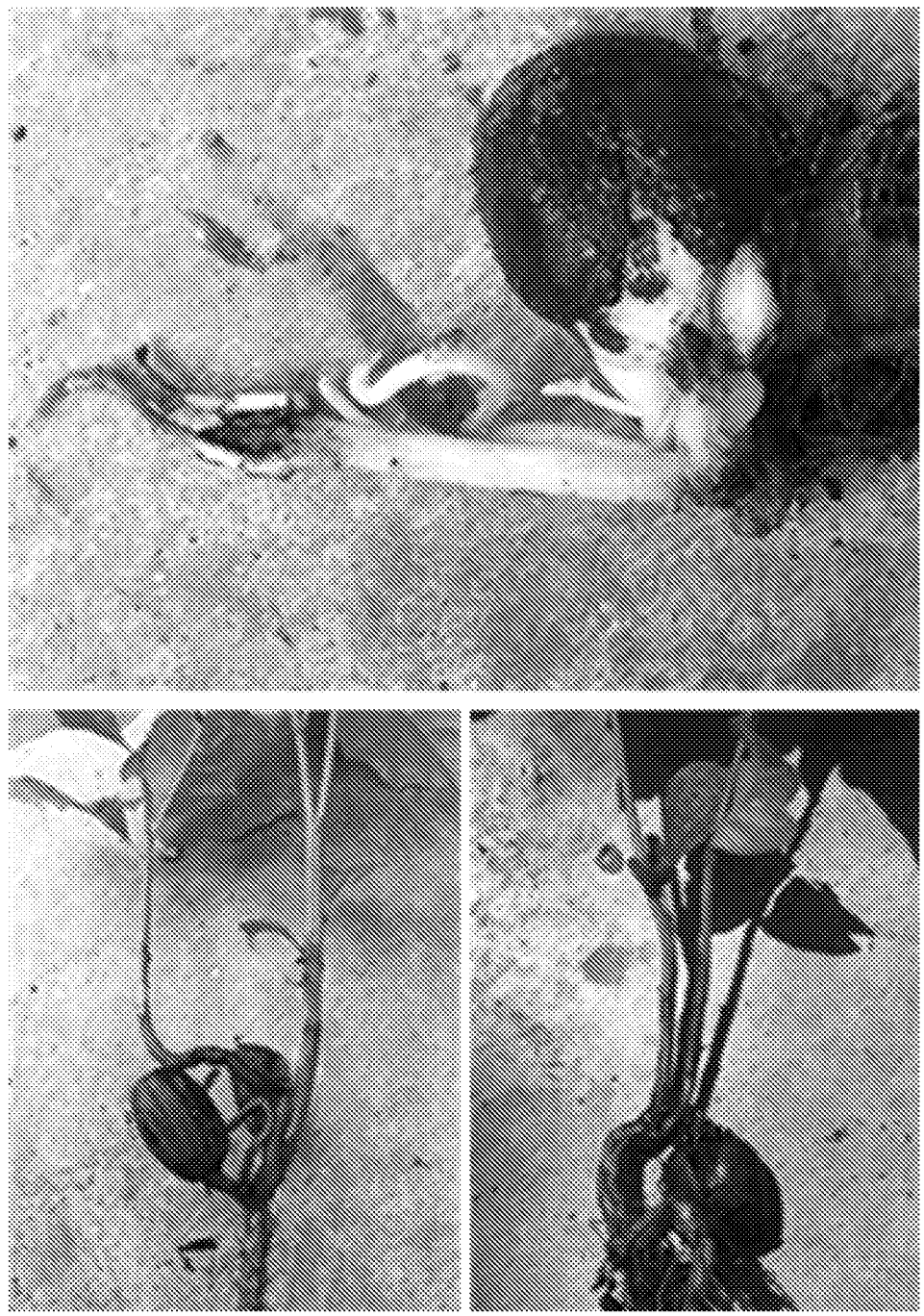
FIG. 8—About 18% of the germinated acorns of *Quercus shumardii* developed multiple stems after the acorns soaked in a treatment of 5% *Q. shumardii* acorn extracts.
Figure 9:
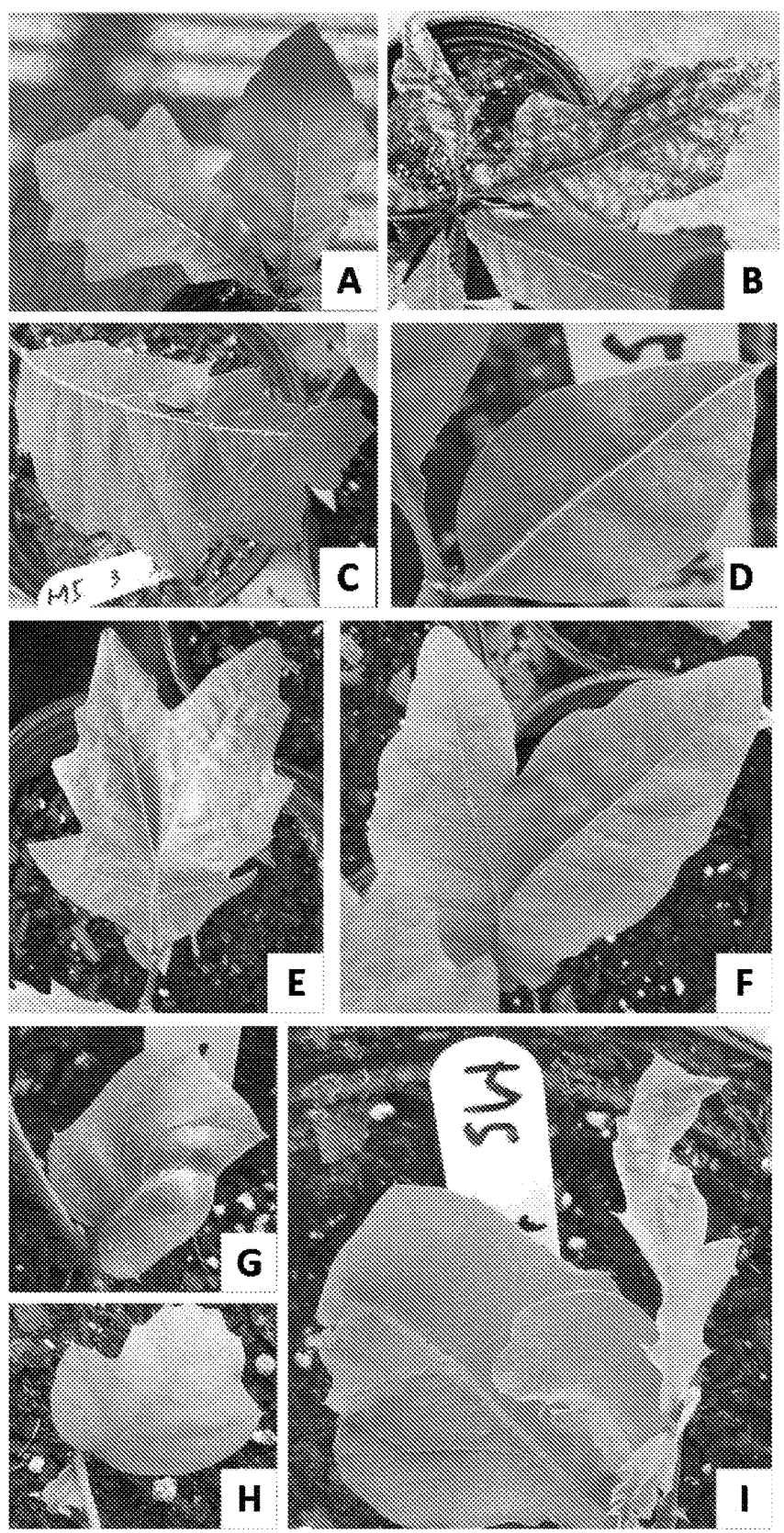
FIG. 9A-9I—Abnormal leaf morphogenesis developed in the early leaves of *Quercus shumardii* after the acorns soaked in 5% ethanol extracts of *Q. shumardii* acorns (B-I) in comparison with normal leaves (A).

As non-limiting examples, a seedling *A. hypogaea* germinated from a seed soaked in 5% *A. hypogaea* nutshell extracts developed abnormal leaf morphogenesis including one or three developed leaflets (vs. normal four leaflets), lobed leaves, and flat petioles (FIG. 6B-6D compared to normal growth in FIG. 6A). For *Q. shumardii*, 5% ethanol extracts of acorns induced about 18% of seedlings to develop multiple stems (3-5) (FIG. 8). Further, early development leaves of almost all seedlings in the 0.5% or 5% extracts treatment group displayed abnormal morphogenesis (e.g., lobed leaves, see FIG. 9B-9I compared to normal growth in FIG. 9A).

Usually, plants restored normal leaf morphogenesis in later growth. Interestingly, the abnormal morphogenesis in seedlings (both shrubbiness phenomenon and leaf shapes) caused by long soaking or external applications of acorn extracts are similar to the reduced apical dominance (coppicing and leaf shapes) following decapitation pruning of trees which also induce biosynthesis of endocides.

External application of endocides also induced pleiocotyly in several species as that observed in prolonged seed soaking in water. As a non-limiting example, 13.9% of pleiocotyly was observed in *T. sebifera* seedlings germinated from the seeds soaked in a 5% solution of EtOH extracts from *T. sebifera* seeds for six weeks. Like woody species, herbaceous *B. oleracea* showed shrubbiness, pleiocotyly, and various abnormal leaves in seedlings germinated from seeds soaked in a 5% solution of *B. oleracea* seed extracts for 48 h (FIGS. 10A-10C, 10E, and 10F compared to normal growth in FIG. 10D). Of the 610 *B. oleracea* seedlings germinated from the 900 seeds soaked in a 5% solution of seed extracts for 48 h, approximately 1.3% developed 2-5 stems directly from the same radicle, approximately 1% had pleiocotyly, and approximately 3.5% had various abnormal leaf morphogenesis including leaves with two lobes or leaves with leaflets on surface. Following the 48 h water soaking, no seedling developed with multiple-stems or pleiocotyly and less than 0.5% of seedlings developed with an abnormal leaf. This is a lower mutation rate than the results observed in seedlings soaked in extract.

External application of endocides also induced mutations in *S. molesta* plants. It is disclosed herein that type I and type II of *S. molesta* can be induced in normal (type III) *S. molesta* plants by endocides. The induced type of new growth in *S. molesta* is determined by the endocidal effects on the plant. A type II of new growth will be induced from either apical or axillary buds of type III *S. molesta* plants when moderate level of endocides are available, e.g., by direct application of endocides (Example 12) or enhanced production of endocides due to severe physical damages (e.g., fragmenting to remove most or all leaves from the buds) (Examples 12 and 13). However, when a higher level of endocide is available, only type I of new growth will develop from any types of *S. molesta* plants, e.g., enhanced production of endocides in the surviving propagules due to severe damage, endocides released after all floating leaf tissues die, external applications of high level of endocides, or both (Example 12). With no disturbance or with slight damage, type III *S. molesta* plants develop type III new growth only (Example 13). Some type I plants never grow into type II or type III plants, particularly when higher levels of endocides are available. 4-Hydroxybenzoic and 3,4-dihydroxybenzoic acids, two compounds isolated from *S. molesta*, induced such mutations in *S. molesta* at lower concentrations (e.g., <1%) (Example 12). However, each of these compounds alone can also eliminate some *S. molesta* plants, particularly at higher concentrations (>0.5%) (Example 14). At the same application dosage, the combination of these two compounds was more effective than either one alone in control of *S. molesta* (Examples 14 and 17). In the field trials, each of these endocidal compounds alone or in combination selectively killed large *S. molesta* plants (type III) in dense mats on the water surface (Example 16). In the field tests, each of these endocidal compounds alone or in combination also selectively killed *S. molesta* plants of type I and II on the water surface within 48 h (Example 17). It was found the endocides were more effective in killing type I or II salvinias on the water surface when combined with DAWN® dish soap (e.g., (Example 16). However, the compounds or combination with or without surfactant effectively eradicated the salvinias on the soil or the edge of water bodies (Example 17). If the level of externally applied endocides or available endocides from dead tissues is too high, all tissues will be killed and there will be no regrowth or any growth type induced. It has also been found that 4-hydroxybenzoic and 3,4-dihydroxybenzoic acids can also effectively control *Azolla* but did not affect many other non-related species. However, these compounds did not induce mutation or injury in non-related species. These compounds are referred to as "salvinicides" herein.

Non-limiting examples of endocides include plant matter, extracts of plant matter, and compounds such as, but not limited to:

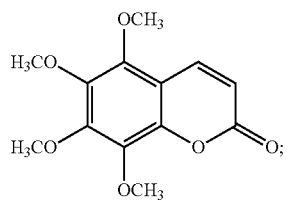

(5,6,7,8-tetramethoxycoumarin)
identified from *T. sebifera* extract

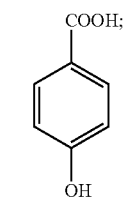

4-hydroxybenzoic
acid from
*S. molesta* extract

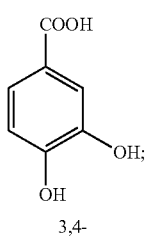

3,4-
dihydroxybenzoic
acid from
*S. molesta* extract

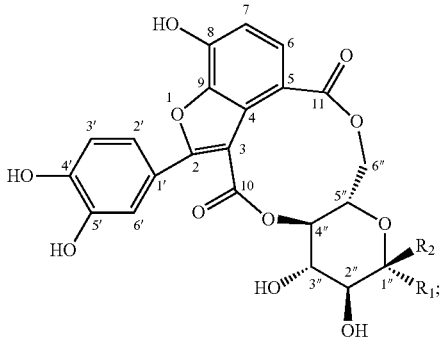

$R_1 = OH, R_2 = \beta\text{-H or}$
$R_1 = \alpha\text{-H}, R_2 = OH$
both identified from
*S. molesta* extract

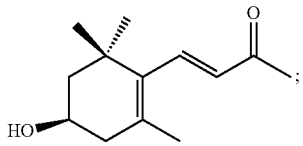

((+)-3-hydroxy-β-ionone)
identified from
*S. molesta* extract

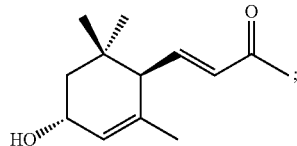

((3R,6R,7E)-3-hydroxy-4,7-
megastigmadien-9-one)
identified from
*S. molesta* extract

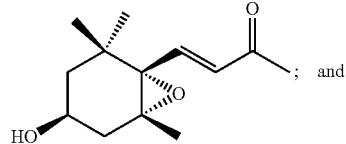

; and (annuionone D) is identified from
*S. molesta* extract

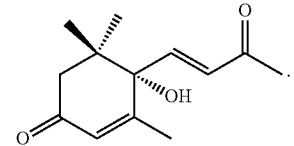

(dehydrovomifoliol) identified
from *S. molesta* extract

As disclosed herein 4-hydroxybenzoic acid and 3,4-dihydroxybenzoic acid has been shown to be an effective endocide against and can induce mutations in *S. molesta* and/or *Azolla caroliniana*. 4-Hydroxybenzoic acid, 3,4-dihydroxybenzoic acid, and some other phenolic acids were reported as the main autotoxins in tobacco (Yu, Liang et al. 2014; Yu, Shen et al. 2014) and 4-hydroxybenzoic, and other phenolic acids from root exudates of tobacco showed some inhibitory activity on growth and photosynthetic rate in tobacco (Zhang, Xu et al. 2013) (Wang, Li et al. 2014). 4-Hydroxybenzoic acid was also identified as one of the autotoxins in cowpea (Huang, Bie et al. 2010) and 4-hydroxybenzoic acid, 3,4-dihydroxybenzoic acid, and some other phenolic acids reportedly are found in and inhibit some growth of dihuang (Li, Yang et al. 2012).

However, the reported activities of these compounds are contradictory. 4-Hydroxybenzoic acid showed weaker inhibitory activity than benzoic acid on the growth of taro (Asao, Hasegawa et al. 2003) and weaker than adipic acid in growth of some leaf vegetables (Asao, Kitazawa et al. 2004). Kim et al. found that the main chemical constituents in water extracts of *Phytolacca Americana* leaves are phenolic compounds that include 3,4-dihydroxybenzoic acid and this extract exhibited allelopathic effects on *Lactuca uindica* and *Sonchus oleraceus* (Kim, Johnson et al. 2005). However, the extracts had little effects on seed germination of (*P. americana*) (Kim, Johnson et al. 2005) and extracts of two other *Phytolacca* species (*P. esculenta* and *P. insularis*) that contained similar level of 3,4-dihydroxybenzoic acid as *P. Americana* can, in contrast, slightly stimulate the germination of *L. uindica* and *S. oleraceus* at lower concentration (Kim, Johnson et al. 2005). These results indicated that 3,4-dihydroxybenzoic acid is not the active compound responsible for the phytotoxicity of *P. americana* extracts. Additionally, Wu et al. reported that 3,4-dihydroxybenzoic acid can increase the root mass of king protea explants at 100 mg/L but inhibit growth at 500 mg/L in MS medium culture (Wu 2006; Wu, du Toit et al. 2007). However, their data did not support the conclusion as Table 1 in both documents showed no significant difference after the 3,4-dihydroxybenzoic acid treatment at 500 mg/L in comparison with no treatment in either mean root length or fresh mass weight. Further, the king protea explants had no significant difference after treatment at 100 mg/L in comparison with no treatment in mean root length, but had significant difference in mean root fresh mass weight. Thus, the data of Wu et al. (2007) actually showed that 3,4-dihydroxybenzoic acid had no significant impacts on the root growth of king protea explants in MS medium culture.

Further, reports of antimicrobial activity of phenolic acids, including 4-hydroxybenzoic acid are consistent with the growing belief that autotoxicity is primarily caused by the indirect effects of autotoxins via influencing microbes or parasitic organisms in the environment. For example, 4-hydroxybenzoic acid has been shown to decrease the Shannon-Wiener index for the rhizosphere bacterial population but increase that for the rhizosphere fungal populations (Zhou, Yu et al. 2012), stimulate the mycelial growth of *Fusarium oxysporum* f. sp. *niveum*, a fungal pathogen of watermelon (Liu, Xu et al. 2011), promote the hypha growth and spore proliferation of *F. oxysporum, F. nivale, Aspergillus flavus*, and *A. fumigatus* but also upgrade the expression of signal transduction system and nutrition metabolization related genes (Li 2012). 4-Hydroxybenzoic acid also inhibited both anthracnose pathogen and N-fixing bacteria in peanut at high concentrations (Liu, Gao et al. 2012) but stimulated the growth of Enterbacter *ludwigii*, a bacterial pathogen in the rhizosphere soils of Tai Zi Shen (Dai 2012).

However, disclosed herein, 4-hydroxybenzoic acid and 3,4-dihydroxybenzoic acid has now been shown in multiple experiments to be an effective endocide against and can induce mutations in *S. molesta* and/or *Azolla caroliniana*.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

It is expected that the methods disclosed herein are capable of inducing mutations in a broad range of species. Further, it is expected that in some instances, an endocide is capable of inducing mutations in a broad range of species, in mammals, and/or in humans. It is also expected that in some instances, an endocide is capable of inducing mutations only in the species from which the endocide was derived or also in closely related species.

EXAMPLES

Herein is disclosed that endocides induced mutations in plants that include, but are not limited to, shrubbiness or dwarfism, pleiocotyly (multicotyledonous), abnormal leaf morphogenesis particularly leaf teeth or lobe development, and/or chemical biosynthesis and derivatization. Also disclosed herein is that 4-hydroxybenzoic acid, 3,4-dihydroxybenzoic acid, a derivative thereof, and/or an analogue thereof, or any combination thereof are endocides against species in the order of Salviniales, such as *Salvinia molesta* and *Azolla caroliniana*.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mutations of Woody Plants Induced by Decapitation Pruning

Mutations Induced by Decapitation
Experimental Procedure:

Six mature plants in the field in Nacogdoches, Tex., United States were selected from each of the nine species with various simple leaves and one species with compound leaves listed in the Table 1. The simple-leaf species include seven tree species *C. acuminata, C. lowreyana, T. sebifera, M. alba, L. styraciflua, Q. shumardii*, and *P. persica*, one shrubby species *I. vomitoria*, and one woody vine species *E. pungens*. The compound-leaf species is *S. canadensis*. The compound-leaf species was *Sambucus Canadensis* L. (Adoxaceae). Three plants from each species were served as control without any treatment. All main stems of the rest three plants from each species were removed from above ground at about 15-30 cm in December. First five newly developed leaves in each pruned plant were surveyed and photographed in March of the next year. Camptothecin (CPT) contents of the leaves in both pruned and unpruned trees were analyzed by the established method (Li et al., 2002).

Results:

In all treated plants of seven tree species, two shrubby species, and one woody vine species, at least one of the following mutations were observed after the pruning: serrated or lobed leaves, bifid, or trifid leaves, compound leaves (e.g., two leaflets per petiole), disturbed phyllotaxis, fasciated stems, or variegation (FIG. 2A-2J). In addition to the lobed, bifid, or trifid leaves, it was observed that *S. canadensis* plants produced twice pinately compound leaves with 3 leaflets (vs. normal once pinately compound leaves with 5-11 leaflets) after pruning treatment.

Example 2

Development of Lowrey's Happytree (*Camptotheca lowreyana* S.Y. Li) Cultivars by Unconventional Prolonged Fruit Soaking in Water General Experimental Procedure:

Fruits of *C. lowreyana* were directly collected from a single parent tree. Randomly selected fruits were divided into two groups with 900 fruits each: The first group of fruits had no treatment and was stored at room temperature (approximately at 20° C.) for nine weeks to serve as control, and the second group of fruits was soaked in water in nine plastic containers separately (100 fruits per plastic container with 100 ml water) at room temperature for nine weeks. Both groups of fruits were then sowed in the pots with soil in greenhouse (30° C. during the day time and 20° C. at night) with daily water for germination. Weekly germination surveys were conducted and the seedlings with abnormal true leaves or stems were documented. All germinated seedlings were transported into large pots for further observation three months after germination. In the next two years, the seedlings with mutated leaves or stems were propagated from hardwood stem by cutting with rooting hormones (in a mist system in greenhouse). CPT contents of the three 3-year old plants of each developed cultivar were analyzed by the established method (Li et al., 2002).

Results:

In the control group, none of 422 germinated seedlings had abnormal leaves in comparison with the seedlings of *C. lowreyana* in field. 23 of the 69 germinated seedlings in the treatment group had mutation in at least one true leaf or stem including leaf size, lobed or bifid leaves, compound leaves (e.g., two leaflets per petiole), disturbed phyllotaxis, fasciated stems, or leaf variegation (with white and green bi-color or mosaic pattern). Two mutated seedlings were successfully propagated by cutting to produce over 150 plants each and were developed as cultivars 'Katie' and 'Hicksii'.

New Varieties Produced by Unconventional Prolonged Fruit Soaking in Water

Figure 3:
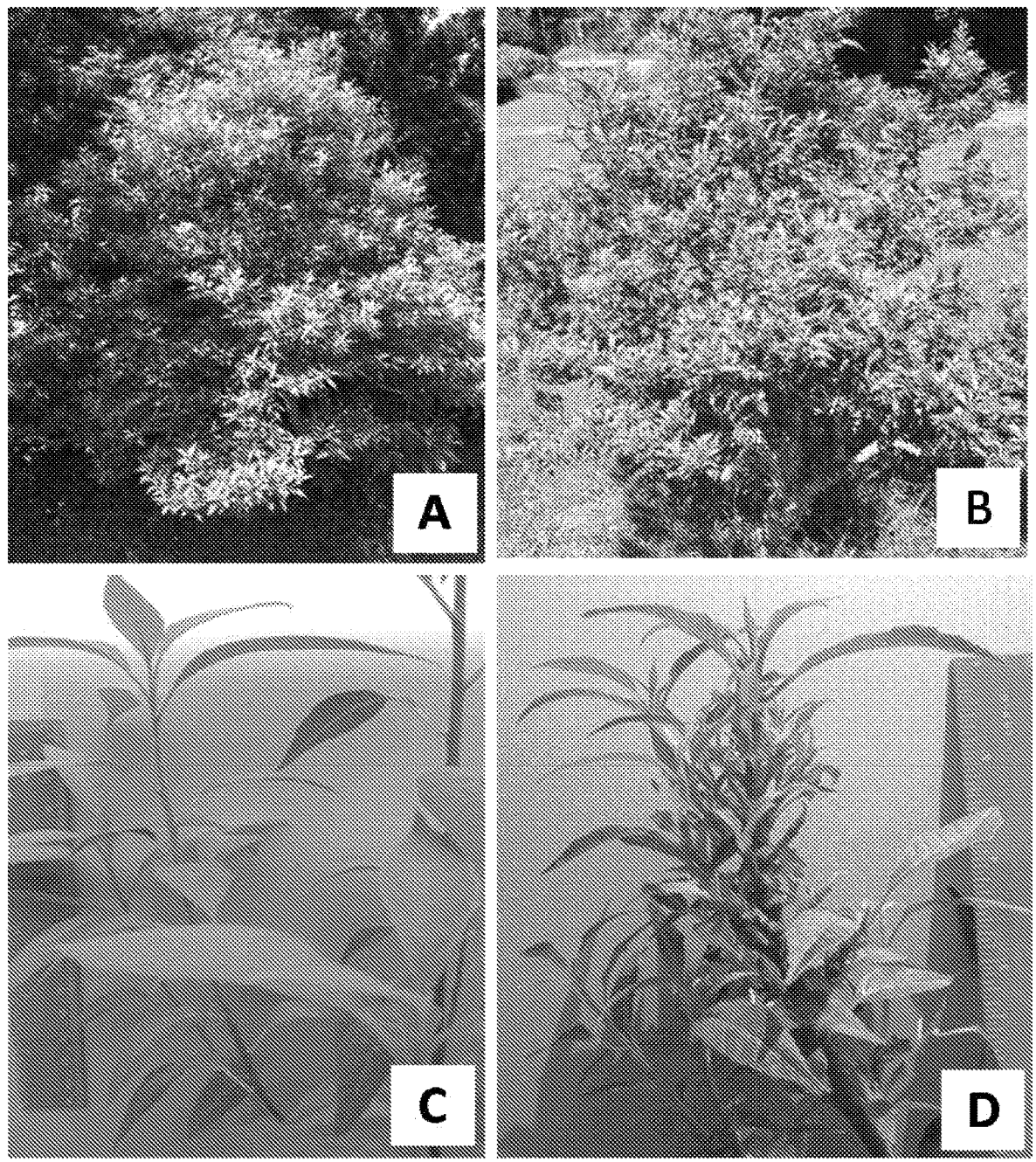
FIG. 3A-3D—*Camptotheca lowreyana* 'Katie' is a shrub cultivar up to 3 m in maturity (A) and has normal small leaves (C). 'CT168' is a dwarf cultivar developed from 'Katie'. It can grow usually up to 1 m in maturity (B) and has fasciated stems, heterogeneous leaves, reduced internodes, and disturbed phyllotaxis (D).

'Katie':

Unlike the parent *C. lowreyana* var. *lowreyana* which can grow up to 20 m in height (FIGS. 3A and 3C), 'Katie' is a shrub with a maximum height of 3 m (FIG. 3B). It has vigorous and dense multi-branching growth habit and smallest and lanceolate or elliptic leaves with entire margins in both juvenile and maturity stages (FIG. 3D). The cultivar has significantly higher CPTs yield with 0.4778% at average (on dry weight basis) in young leaves in comparison with its parent tree (0.3913%). It is also more hardy and drought-tolerant than natural *Camptotheca* taxa.

Figure 4:
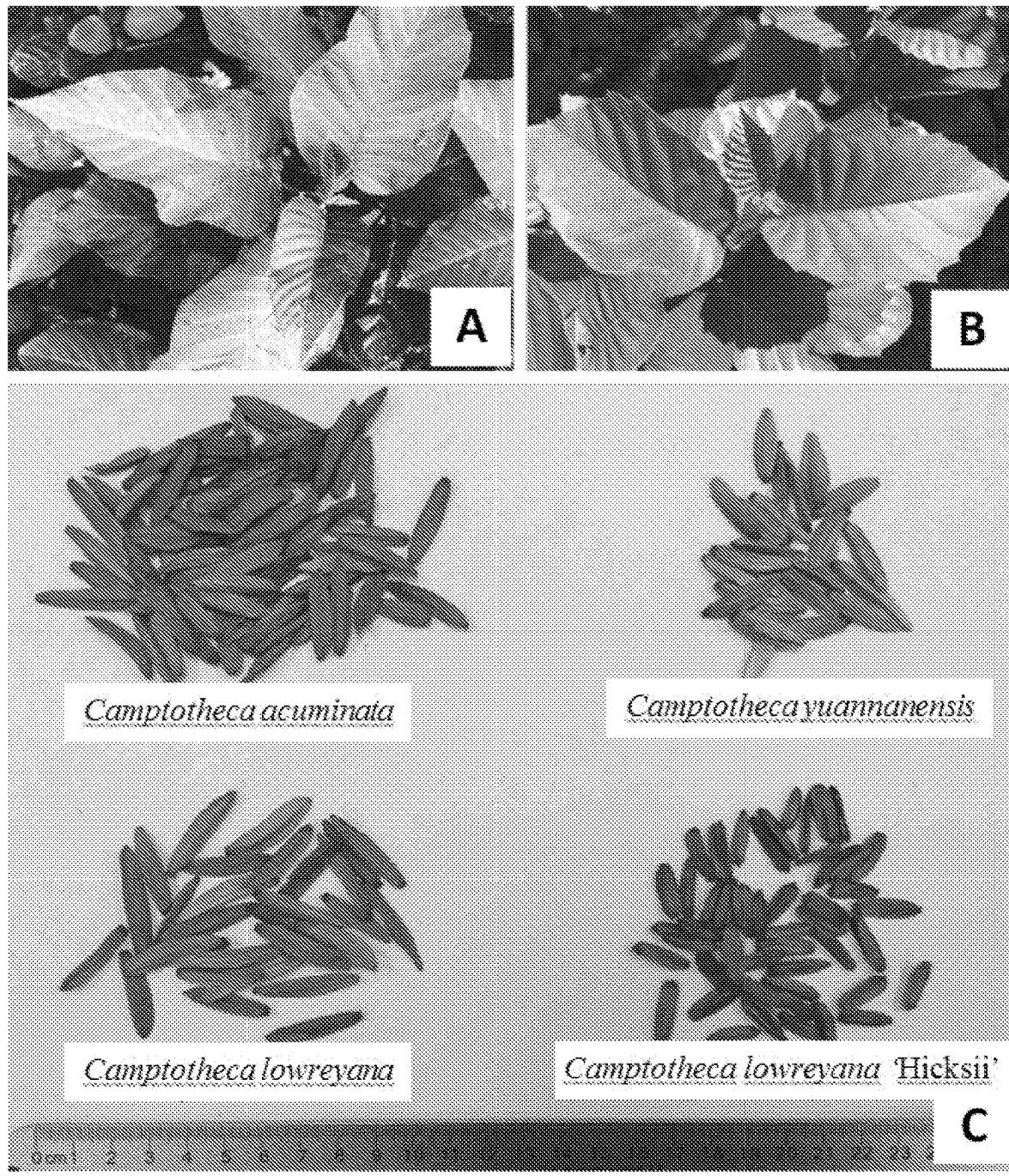
FIG. 4A-4C—Comparison of *Camptotheca lowreyana* 'Hicksii' with its parent *C. lowreyana*: (A.) leaves of mature tree of *C. lowreyana*; (B.) leaves of mature tree of 'Hicksii'; (C.) comparison of mature fruits of with three known species (upper row: left-*C. acuminata* and right-*C. yunnanensis*; bottom row: left-*C. lowreyana* and right-'Hicksii').

'Hicksii':

In 1997, cultivar 'Hicksii' was developed from a shoot cutting of a *C. lowreyana* seedling germinated from a wild seed after prolonged soaking. 'Hicksii' tree cultivar can be distinguished by its smaller and cordate leaves with bigger teeth on margin in both juvenile and mature growth stages from its patent *C. lowreyana* var. *lowreyana* (FIGS. 4A and 4B). The average CPT concentration in young leaves of 'Hicksii' is 0.5537% (on dry weight basis) (Li, 2014). In 2014, fruits were produced from two 15-year-old 'Hicksii' trees. The morphological characteristics of the germinated seedlings are similar and consistent with the parent trees (FIG. 4C). Both vegetative and reproductive characteristics of 'Hicksii' can easily be distinguished from any known taxa (FIG. 4, Table 4).

TABLE 4

Major diagnostic characters of 'Hicksii' from three species of *Camptotheca*

| Major Diagnostic Characters | *C. acuminata* Decaisne | *C. yunnanensis* Dode | *C. lowreyana* Li | *C. lowreyana* 'Hicksii' |
|---|---|---|---|---|
| Leaf Shape | oval/ovaloblong | elliptic | cordate/ovate | cordate |
| Fruit Color (dry) (RHS Color Chart) | red brown or greyed-orange (167 D) | gray or greyed-orange (164 B) | Gray-brown or greyed-orange (164 C) | brown (200 D) |
| Fruit Length (mean ± s.d., mm) | 22.23 ± 2.90 | 20.63 ± 2.03 | 29.73 ± 3.07 | 14.82 ± 4.35 |
| Fruit Disc Thickness | thick | thin | thin | thin |
| Fruit Surface (dry) | rugose | smooth & lucid | smooth & lucid | smooth & lucid |
| Cotyledon Length (mean ± s.d., mm) | 36.21 ± 5.81 | 26.92 ± 3.29 | 34.29 ± 4.93 | 22.36 ± 5.07 |

Example 3

Mutations of Happytrees (*Camptotheca*) Induced by Unconventional Prolonged Fruit Soaking in Water General Experimental Procedure:

Experimental fruits of *C. acuminata* and *C. lowreyana* were collected from single parent trees. 30 untreated fruits of each taxon were directly sowed in the pots in greenhouse to serve as control. 30 fruits of each taxon were soaked in a petri dish in water at room temperature (approximately at 20° C.) for 24 h and 30 fruits of each taxon were soaked under the same conditions four weeks. The soaked fruits were then sowed in the pots in greenhouse. Each of the control and soaking treatment experiments had three replications. Weekly germination surveys were conducted and the seedlings with one or more abnormal true leaves were documented. By the end of two months, the total germinated seedling number of each control or treatment and the number of seedlings with two or more stems derived directly from the fruit and branch number above the soil surface were counted.

Results:

For both taxa, the fruits soaked in water for 24 h had much better germination rate than either those without treatment or soaked in water for four weeks. Following the fruits soaked in water for four weeks, 15.6% *C. acuminata* seedlings developed 2-3 branches compared to no branch development from the fruits with 24 h of soaking or no soaking treatment and 38.5% seedlings of *C. lowreyana* had 2-5 branches from the main stem in comparison with no branch development in those germinated from the fruits with 24 h of soaking or no soaking treatment.

Example 4

Development of New *Camptotheca lowreyana* Variety 'CT168' by Pruning

Experimental Procedure:

During the cultivar development of 'Katie' (see Example 2), repeated pruning of the original mutated seedling of *C. lowreyana* 'Katie' were made to have cuttings propagated. The repeated pruning directly induced the mutation in a stem of the original seedling of 'Katie'. The mutated stem had reduced internodes and smaller leaves. The mutated stem was propagated by cutting without hormones in the mist system in greenhouse (30° C. during the day time and 20° C. at night). In the next three years, repeated propagation by cuttings was made from the rooted plants with rooting hormones or without hormones. CPT contents of the three 3-year old plants of each developed cultivar were analyzed by the established method (Li et al., 2002).

Results:

Over 200 plants were propagated from the mutated stem of 'Katie' by cuttings. The plants propagated with hormones restored its morphological characteristics of its parent 'Katie'. Those propagated by cuttings without any hormones had smaller heterogeneous leaves, reduced internodes, and profuse branching (FIG. 3D). This dwarf mutant, cultivar 'CT168,' of cultivar 'Katie' can grow up to 1 m only in maturity (Li, 2014) (FIG. 3B). 'CT168' has the highest CPT yield in young leaves among known *Camptotheca* taxa (0.5890%).

Example 5

Development of Shrubby Oaks (*Quercus*) by Unconventional Prolonged Acorn Soaking in Water General Experimental Procedure:

Acorns of *Q. shumardii*, *Q. texana*, and *Q. michauxii* were collected from Nacogdoches, Tex., United States. Every species had 30 sound acorns in each of the following two treatments with three replications per treatment: control (no soaking treatment) and soaking in water (just adequate water to cover all acorns) for 48 h in room temperature and then continued soaking in refrigerator (4° C.) for four weeks. The acorns were sowed in the pots with Miracle Grow Potting Mix soil in greenhouse (30° C. during the day time and 20° C. at night). The seedling number with multiple stems (2-3 stems) derived directly from the same radicle in the germinated seedlings was surveyed.

Results:

By the end of four months, no seedlings with multiple stems were observed in the seedlings germinated from acorns without soaking treatment. For the soaked acorns, the percentage of plants developing 2-3 stems directly from the same radicle (shrubbiness) in the germinated seedlings of *Q. shumardii*, *Q. texana*, and *Q. michauxii* were 7.32, 8.64, and 19.27%, respectively (FIG. 5). Other mutations observed in the treated oaks were bilobed leaves, bifid leaves, and variegated leaves in a mosaic pattern.

Example 6

Mutations in Peanut (*Arachis hypogaea*) Induced by its Extracts and Unconventional Prolonged Soaking in Water General Experimental Procedures:

The seeds of *A. hypogaea* were purchased from Royal Oak Peanuts/Hope & Harmony Farms, Drewryville, Va. 500 g dried pod shell and 1,500 g dried seeds (nuts) without sell were ground separately to coarse powders and extracted two times for 48 h with 95% EtOH (4.5 L and 2.5 L each, respectively) at room temperature. Extracts were evaporated under reduced pressure, and 23.4 g shell extracts and 31.2 g seed extracts were obtained. 10 g each of the EtOH extracts were dissolved and suspended in NANOPURE™ $H_2O$ and prepared separately as 200 mL experimental solution at the concentration of 5%. The seed soaking treatment experiments were conducted in NCPC Lab at room temperature. 30 *A. hypogaea* fruits can produce at least 0.83 g shell EtOH extracts and 12.47 g seed EtOH extracts using a ASE 2000 Accelerated Solvent Extractor (60° C., 1500 psi, 30 min static time, 100% volume flush, 120 s purge, and 2 cycles). 360 seeds in total were prepared and 30 seeds in a plastic container (14×15 cm, 0.68 L) were subjected to one of the four treatments for one week with three replications per treatment: (1) control: without any treatment and seeds were directly sowed in the pots; (2) soaked in 60 mL NANOPURE™ $H_2O$; (3) soaked in a 60 mL 5% solution of *A. hypogaea* shell extracts (3 g shell extracts); and (4) soaked in a 60 mL 5% solution of *A. hypogaea* seed extracts (3 g seed extracts). All experimental seeds were sowed in the pots with Miracle Grow Potting Mix soil in greenhouse (30° C. during the day time and 20° C. at night). The morphological variations of each seedling were recorded weekly throughout the experimental period of three months.

Results:

By the end of the experiment, the seeds soaked in 5% solution of *A. hypogaea* seed extracts had not germinated. Four of the seven seedlings germinated from the seeds treated by 5% *A. hypogaea* peanut shell extracts and one of the 20 seedlings in the water soaking treatment had significant abnormal leaf development (e.g., one or three leaflets, petioleless smaller leaflets with non-entire leaf margins, or variegated leaves) and fused stems in comparison with the normal development of leaves (e.g., four leaflets, larger leaflets with entire margin) and stems among the 66 seedlings in the control (FIG. 6B-FIG. 6D compared to normal growth in FIG. 6A).

Example 7

Pleiocotyly in Chinese Tallow (*Triadica sebifera*) Small) Induced by its Extracts and Unconventional Prolonged Soaking in Water General Experimental Procedure:

The leaves and stems of *T. sebifera* were collected from Nacogdoches, Tex., in October 2014 and were dried in an oven at 65° C. for 48 h. 11 kg dried leaves and stems were ground to coarse powders and each were extracted two times for 48 h with 95% EtOH (40 L and 24 L, respectively) at room temperature. Extracts were evaporated under reduced pressure. 410 g EtOH extracts were obtained and then stored in 4° C. The seeds of *T. sebifera* were collected from Nacogdoches, Tex., in October 2014 and were dried in an oven at 65° C. for 48 h. 110 g dried seeds were ground to coarse powders and extracted two times for 48 h with 95% EtOH (500 mL and 400 mL, respectively) at room temperature. The EtOH extracts were evaporated under reduced pressure. 6.3 g extracts were obtained and then stored in 4° C. 60 *T. sebifera* seeds can produce at least 2.11 g EtOH extracts using an ASE 2000 Accelerated Solvent Extractor (60° C., 1500 psi, 30 min static time, 100% volume flush, 120 s purge, and 2 cycles). Both leaf and stem extracts and seed extracts were prepared as experimental solution with NANOPURE™ $H_2O$ at 5% concentration each. A total 900 seeds were prepared for the five following treatments and each treatment included 60 seeds in petri dishes at 20° C. with three replications per treatment: (1) control: without soaking treatment, (2) water-24 h: soaked in 30 mL NANOPURE™ $H_2O$ for 24 h, (3) water-6 weeks: soaked in 30 mL NANOPURE™ $H_2O$ for six weeks, (4) 5% stem extracts-6 weeks: soaked in a 30 mL 5% solution of EtOH extracts of *T. sebifera* leaves and stems for six weeks, and (5) 5% seed extracts-6 weeks: soaked in a 30 mL 5% solution of EtOH extracts of *T. sebifera* seeds (1.5 g extracts) for six weeks. Seeds were sowed in 2-gallon pots with Miracle Grow Potting Mix soil in the greenhouse (30° C. during the day time and 20° C. at night). The number of germinated individuals and cotyledon number were recorded once every week throughout the experimental period. The germination rate and pleiocotyly rate were determined for each replicate.

Results:

No seedling germinated from the *T. sebifera* seeds treated by 5% *T. sebifera* leaf and stem extracts during the eight weeks of experiment. For the seeds treated in 5% *T. sebifera* seed extracts for six weeks, 20% were germinated and 13.9% of the seedlings were pleiocotyly (3 or 4 cotyledons and cotyledons with two lobes). For the seeds soaked in water for six weeks, the germination rate was 57.8% and 10.6% of the seedlings were pleiocotyly (3-4 cotyledons) (FIG. 7 left and right figures compared to normal growth in middle figure). The seeds soaked in water for 24 h had 28.9% germination with 1.9% pleiocotyly among the germinated seedlings. The seeds without soaking treatment had 40.6% germination and no pleiocotyly was observed in any germinated seedlings.

Example 8

Development of Mutated Shumard Oak (*Quercus shumardii*) Plants by Application of Shumard Oak Extracts General Experimental Procedure:

Acorns of *Q. shumardii* were dried in an oven at 65° C. for 48 h. 1 kg dried acorns were ground to coarse powders and extracted two times for 48 h with 95% EtOH at room temperature. Extracts were evaporated under reduced pressure. 50 g EtOH extracts were obtained. The extracts were prepared as experimental solutions with NANOPURE™ $H_2O$ at 0.5 and 5% concentration, respectively. 30 *Q. shumardii* acorns can produce at least 18.96 g EtOH extracts using a ASE 2000 Accelerated Solvent Extractor (60° C., 1500 psi, 30 min static time, 100% volume flush, 120 s purge, and 2 cycles). A total 270 acorns were prepared for the five following treatments and each treatment included 30 acorns in a plastic container (14×15 cm, 0.68 L) at 20° C. with three replications per treatment: (1) control: no soaking treatment, (2) soaked in a 0.5% solution of *Q. shumardii* acorn EtOH extracts (0.75 g acorn extracts) for 48 h, and (3) soaked in a 5% solution of *Q. shumardii* acorn EtOH extracts (7.5 g acorn extracts) for 48 h. The acorns were then sowed in the pots with Miracle Grow Potting Mix soil in greenhouse (30° C. during the day time and 20° C. at night). Survey of seedlings was conducted three months later.

Results:

For *Q. shumardii*, 5% EtOH extracts of acorns induced about 18% of seedlings to develop multiple stems (3-5) in comparison with one stem only in the control (no soaking treatment) (see FIG. 8). Further, early leaf development leaves of almost all seedlings in the 0.5% or 5% extracts treatment group displayed abnormal morphogenesis (e.g., lobed or bifid leaves or variegated leaves (see FIG. 9B-9I)).

Example 9

Development of Mutated Broccoli (*Brassica oleracea*) Plants by Application of Broccoli Extracts General Experimental Procedure:

The seeds of *B. oleracea* were dried in an oven at 65° C. for 48 h. 120 g dried seeds were ground to coarse powders and were extracted two times for 48 h each with 95% EtOH (400 mL each time) at room temperature. Extracts were evaporated under reduced pressure. 4 g EtOH extracts were obtained and then stored in 4° C. 1.5 g *B. oleracea* seed extracts were dissolved in NANOPURE™ $H_2O$ and prepared as 30 mL experimental solution at the concentration of 5%. 300 *B. oleracea* seeds can produce at least 0.1 g EtOH extracts using a ASE 2000 Accelerated Solvent Extractor (60° C., 1500 psi, 30 min static time, 100% volume flush, 120 s purge, and 2 cycles). 1,800 *B. oleracea* sound seeds were selected and 300 seeds in a Petri dish were subjected to one of the following soaking treatments for 48 h at room temperature with three replications per treatment: a 10 mL NANOPURE™ $H_2O$ (to serve as control) and a 10 mL 5% solution of *B. oleracea* seed extracts (0.5 g extracts). Seeds were sowed in germination box with Miracle Grow Potting Mix soil (50 seeds per box) in the greenhouse (30° C. during the day time and 20° C. at night). The number of germinated individuals and cotyledon number, leaf morphology, and stem number were recorded once every week throughout the 4-week experimental period.

Figure 10:
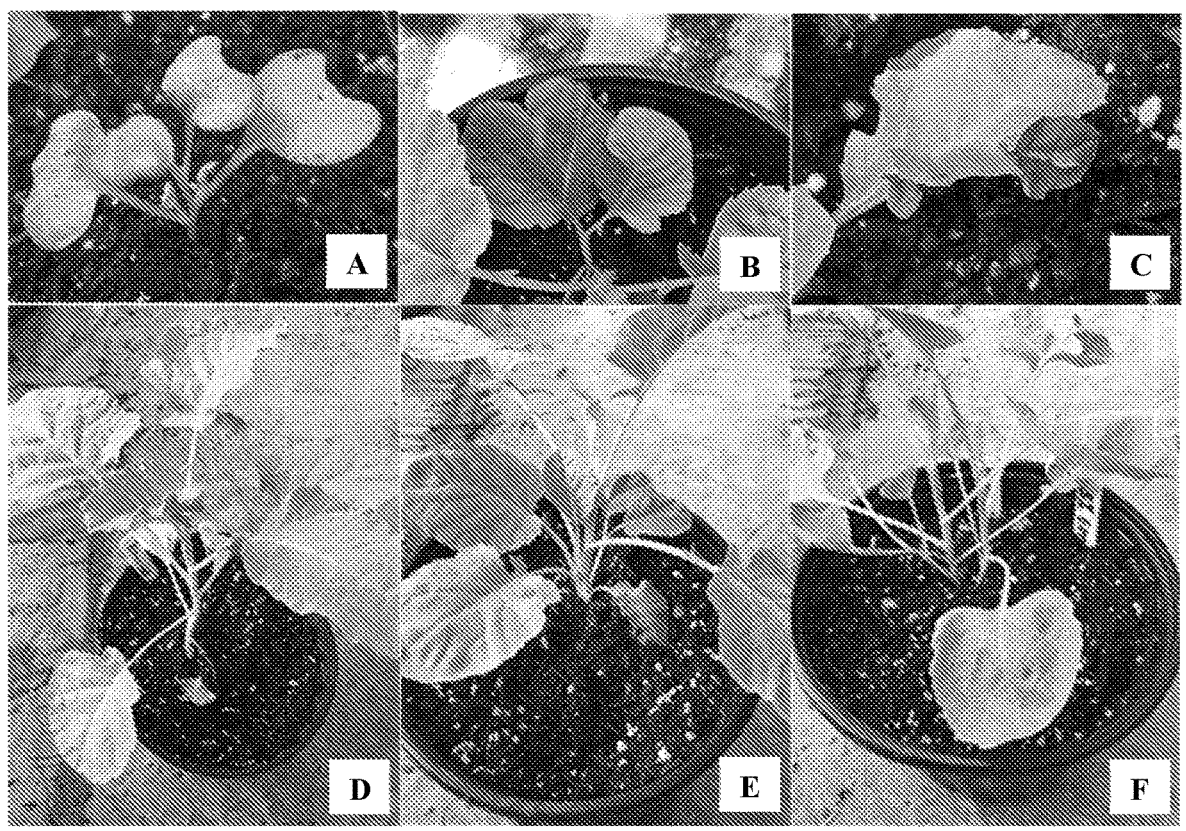
FIG. 10A-10F—Induced mutations in *Brassica oleracea* by soaking the seeds in a 5% solution of EtOH extracts of *B. oleracea* seeds for 48 h. (A) abnormal pleiocotyly (4 cotyledons). (B) leaf with two lobes. (C) leaflet on leaf (D) normal single stem seedling without treatment. (E and F) induced shrubbiness with two more stems.

Results:

Of the 610 *B. oleracea* seedlings germinated from the 900 seeds soaked in a 5% solution of seed extracts for 48 h, approximately 1.3% developed multiple-stems (2-5) directly from the same radicle (shrubbiness), approximately 1% had pleiocotyly (3-4 cotyledons), and approximately 3.5% had various abnormal leaf morphogenesis including leaves with two lobes or with leaflets on surfaces (FIGS. 10A-10C, 10E, and 10F compared to normal growth in FIG. 10D). In the 48 h water soaking treatment, no seedling developed with multiple-stems or pleiocotyly and less than 0.5% seedlings developed with an abnormal leaf (but significantly lower from that observed in seedlings induced by the extracts).

Example 10

Development of Muted Nopal Cactus (Opuntia Ficus-Indica) Plants by Application of Nopal Cactus Extracts Extraction Procedures The fleshy oval stems (pads or paddles) of O. ficus-indica (300 g in dry weight) were ground to a coarse powder and extracted two times for 48 h each with 95% EtOH (1.2 L each time) at room temperature. The combined extracts were concentrated under reduced pressure to give 16.6 g. 5 g of extracts were dissolved in NANOPURE™ $H_2O$ and prepared as a 100 mL experimental solution at the concentration of 5% EtOH extracts of the O. ficus-indica. Six O. ficus-indica stems can produce at least 4.93 g EtOH extracts based on the above extraction experiment.

Soaking Experiment:

12 pieces of O. ficus-indica stems (15-17 cm) were prepared and subjected to two treatments. Six O. ficus-indica stems were cultivated in 100 mL NANOPURE™ $H_2O$ to serve as control and six stems were cultivated in 100 mL 5% EtOH extracts of O. ficus-indica (5 g extracts) for 12 days at room temperature.

Growth and Propagation Tests:

Each experimental O. ficus-indica stem was placed in a one-gallon pot with Miracle Grow Potting Mix soil in the greenhouse. The living status of individuals was recorded once every week throughout the experimental period.

Results:

By the end of the second month, all stems of O. ficus-indica in the control group were alive and showed normal growth and development. At the same time, two of the six stems treated with O. ficus-indica extracts survived but developed larger leaves (1.5 to 2.5 cm long) and some mutated enlarged leaves were retained on new stems for several months. Usually, the leaves of O. ficus-indica are minute and are shed early in the normal development process.

Example 11

Chemical Biosynthesis and Derivatization in Mutated Leaves of Shumard Oak (Quercus shumardii) Seedlings Induced by Application of Shumard Oak Extracts General Experimental Procedures:

The acorns of Q. shumardii were collected from a tree grown in Nacogdoches, Tex., United States. For acorn treatments see Example 8. One leaf was randomly collected from each of the two two-month-old normal seedlings, and one normal leaf and one bi-lobed leaf were collected from each of the two abnormal seedlings induced by 0.5% EtOH extracts of Shumard oak acorns. The samples of acorns and leaves were dried in an oven at 65° C. for 48 h. The dried samples were weighed and ground. An ASE 200 Accelerated Solvent Extractor (Dionex Corp., Sunnyvale, Calif.) was used to extract the EtOH extracts. Each of the leaf samples (0.2 g) and acorn samples (10 g) were loaded in 22 mL cells and a 33 mL cell. 95% EtOH was used as the solvent. The extraction was performed under the following parameters: 60° C., 1500 psi, 30 min static time, 100% volume flush, 120 s purge, and 1 cycle. The 95% EtOH extracts were evaporated under reduced pressure, transferred into the 10 mL volumetric flask, then diluted to volume with 95% EtOH and mixed as experimental solutions. The HPLC chromatographs of oak leaves and acorn extracts were established by Agilent 1100 HPLC system coupled to an Agilent 1100 diode array detector, and an Eclipse XDB-C18 column (4.6×150 mm, 3.5 µM) at a flow rate of 0.6 mL/min. A gradient elution was performed by using $H_2O$ (A) and $CH_3CN$ (B) as mobile phases. Elution was performed according to the following conditions: 2% B at time 0, linear increase to 98% B in 22 min, and hold 98% B for 8 min. The injection volumes were equivalent to 0.34 mg plant material for all analyses. The column temperature was maintained at 23° C. The HPLC chromatogram was standardized on retention times and peak intensities of the peaks observed at a wavelength of 254 nm.

Figure 11:
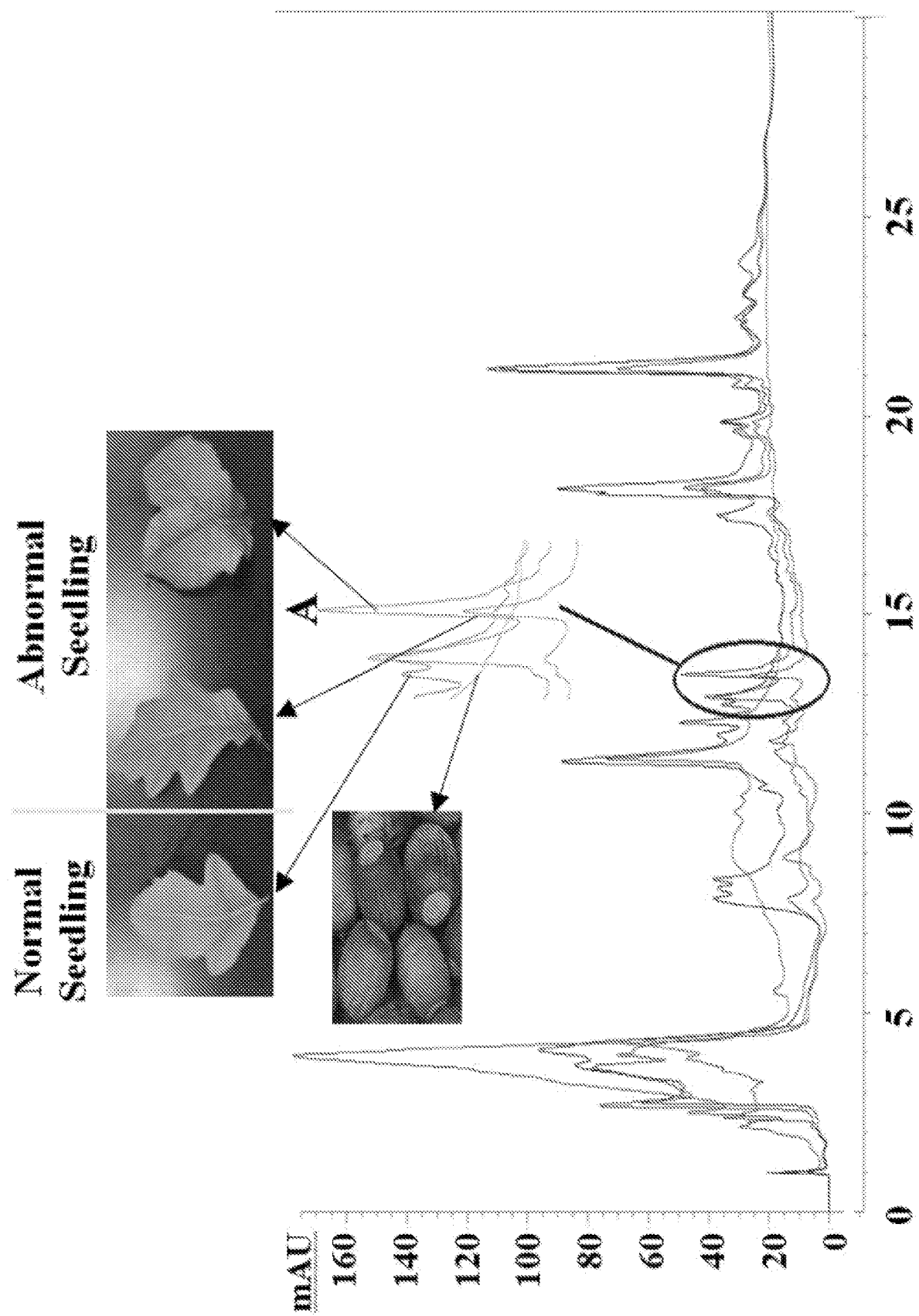
FIG. 11—HPLC profiles of leaf extracts of abnormal seedling of *Quercus shumardii* induced by *Q. shumardii* acorn extracts in comparison with leaf extracts of a normal seedling and acorn extracts. The normal and bi-lobed leaves from the abnormal seedlings are similar in HPLC profiles but both had a compound (A) that was not detected in either acorns or normal seedlings of *Q. shumardii*.

Results:

The HPLC profiles of leaf samples from two normal seedlings are similar each other but significantly different from either normal or bi-lobed leaves from the abnormal seedlings induced by 0.5% EtOH extracts. The chromatographs of the extracts also showed that Q. shumardii acorns had much less chemical diversity than seedlings. Interestingly, the normal and bi-lobed leaves from the abnormal seedlings are similar in HPLC profiles but both had a compound that was not detected in either acorns or normal seedlings of Q. shumardii (FIG. 11).

Example 12

Mutations of Giant Salvinia (Salvinia molesta) Plants Induced by 4-Hydroxybenzoic and 3,4-Dihydroxybenzoic Acids Isolated from Giant Salvinia General Experimental Procedure:

4-hydroxybenzoic acid (>95%, HPLC analysis) and 3,4-dihydroxybenzoic acid (>95%) were isolated from S. molesta matter by using the method as described in Li, Wang et al. 2013. 4-Hydroxybenzoic and 3,4-dihydroxybenzoic acids were prepared as 50 mL experimental solution with NANOPURE™ water at eight concentrations, 0.015, 0.031, 0.063, 0.125, 0.25, 0.5, 1, and 2%, respectively.

In each of 17 containers (14×15 cm, 0.68 L each), nine healthy and untreated living plants of S. molesta were cultured in tap water in a greenhouse (30° C. during the day time and 20° C. at night). The nine plants included three type I plants (approximately 1 g in fresh weight per plant), three type II plants (approximately 2 g per plant), and three type III plants (approximately 4 g per plant). The plants in each container were sprayed with 10 mL NANOPURE™ water or an experimental compound at various concentrations. Plant growth, morphological variation, and survival status were documented and photographed in each treatment for six weeks after the treatment. Then any new developed plants in each container were transferred into a container with new water for 10 weeks of culture observations.

Results:

In the control treatment with water only, the experimental S. molesta plants in both type I and II plants grew to the large sizes (type III) after six weeks of culture. The impacts of 4-hydroxybenzoic and 3,4-dihydroxybenzoic acids on S. molesta development depend on their treatment concentrations. In the 1% 4-hydroxybenzoic acid treatment container, all six type I or II plants were dead without new growth within two days of the treatment. By the end of second week after the 1% 4-hydroxybenzoic acid treatment, three small plants (type I) emerged from the axillary buds of the type III plants after all the large floating leaves in these type III plants had died or turned brown. However, the three type I plants experienced slow growth and remained in the form of small, flat, and oval-shaped floating leaves (<10 mm in width) for the following four weeks in the original culture solution. Even after transfer of these three type I plants into another container with new water, these plants failed to turn into type II plants during the additional 10 weeks of observation. All nine *S. molesta* plants in the 2% 4-hydroxybenzoic acid treatment died and showed no new growth during the experiment.

The application of 0.5% 4-hydroxybenzoic acid killed almost all floating leaves of the nine treated plant within a week. By the end of the second week, new floating leaves had emerged from eight plants and one type I plant had died. By the end of the six weeks of experiment, only one type III plant with partial green apical floating leaves had developed slightly cupped leaves (type II), whereas all other newly emerged plants from axillary buds remained as type I during the whole experimental period in the original culture solution. Even after transferring the eight new type I plants into new containers with new water, the growth status did not obviously improve.

The 0.25% 4-hydroxybenzoic acid application killed all floating leaves of the small plants (type I and II) and partially injured floating leaves of the type III plants during the first week. Seven plants developed cupped floating leaves (type II) from apical buds of six type II or III plants and one type I plant by the end of the six weeks of experiment. Two emerged plants from the type I plants remained in the same form during the whole experimental period in the original culture solution. The number and size of floating leaves and submerged root-like leaves and internode length of all nine plants were improved after transferred into a new container.

By the end of the experiment, the *S. molesta* plants treated by 0.125% or lower concentrations had no significant damage. Similar to those in the control group, there were only type III plants observed in these containers by the end of the six weeks of experiment and no induced type I or II plants were observed.

Similar to 4-hydroxybenzoic acid, 3,4-dihydroxybenzoic acid (0.25, 0.5, and 1%) also induced small leaf mutations in *S. molesta*. More new growth was observed following the treatments of 0.5% or 1% 3,4-dihydroxybenzoic acid than the treatments of 4-hydroxybenzoic acid, but the new plants remained as type I during the six weeks of observation. 2% 3,4-dihydroxybenzoic acid treatment killed all of the plants and no new growth was observed.

Example 13

Induction of Growth Types of Giant *Salvinia* (*Salvinia molesta*) Plants by Fragmenting General Experimental Procedure:

The fragmenting experiments of *S. molesta* were conducted in the greenhouse (30° C. during the day time and 20° C. at night) in containers (60×43×15 cm, 27 L) with 20 L tap water. A first container was used to cultivate 30 healthy and untreated intact type III *S. molesta* plants, a second container was used to cultivate 30 apical buds, the fragments were cut from the healthy type III *S. molesta* plants by a knife blade, and a third container was used to cultivate 30 apical buds with two nodes including floating and submerged leaves, the fragments were cut from healthy type III *S. molesta* plants by a knife blade. Plant growth, morphological variation, and survival status were documented and photographed in each treatment three weeks after the treatment.

Results:

Each of the 30 type III intact *S. molesta* plants had type III of new growth from its terminal bud within three weeks of experiments. There were no other types of new growth or lateral stems developed in this group of plants. Seven of the 30 *S. molesta* buds without leaves developed type I of new growth during this period. Each of the 30 *S. molesta* buds with two nodes including floating and submerged leaves developed one to three axillary buds with an average of 2.97 stems (±0.62 (s.d.)) by the end of the experiment. Only type II of new growth emerged from the apical and axillary buds in this treatment.

Example 14

Elimination and Inhibition of Giant *Salvinia* (*Salvinia molesta*) and Carolina Mosquito Fern (*Azolla caroliniana*) Plants in Greenhouse Tests by 4-Hydroxybenzoic and 3,4-Dihydroxybenzoic Acids Isolated from Giant *Salvinia*

General Experimental Procedure:

Observations of giant *salvinia* growth in a greenhouse were performed under 28 different treatment conditions and control conditions with NANOPURE™ water or 0.5% DYNE-AMIC® (methyl esters of C16-C18 fatty acids, polyalkyleneoxide modified polydimethylsiloxane, and alkylphenol ethoxylate 99%, (Helena, Collierville, Tenn., United States)) (v:v).

Materials—4-hydroxybenzoic acid (>95%, HPLC analysis) and 3,4-dihydroxybenzoic acid (>95%) were isolated from *S. molesta* matter using the method as described in (Li, Wang et al. 2013). Ethylparaben (>99%) was purchased from a commercial source. Each of 4-hydroxybenzoic acid, 3,4-dihydroxybenzoic acid, and ethylparaben were prepared as 50 mL experimental solutions with NANOPURE™ water at the concentration of 0.5, 1.0, 1.5, and 2.0%, respectively. 0.5, 1.0, 1.5, and 2.0% 4-hydroxybenzoic acid, 3,4-dihydroxybenzoic acid, and ethylparaben with 0.5% surfactant DYNE-AMIC® was also prepared as 50 mL experimental solutions with NANOPURE™ water. Mixtures of 4-hydroxybenzoic acid with 3,4-dihydroxybenzoic acid (2:1, w:w) were prepared as 50 mL experimental solutions with NANOPURE™ water at the total concentration of 0.5, 1.0, and 1.5%, respectively. 3,4-dihydroxybenzoic acid was mixed with ethylparaben (2:1, w:w) and prepared as 50 mL experimental solution with NANOPURE™ water at the total concentration of 0.5, 1.0, and 1.5%, respectively.

Bioassay—For each treatment, a total of nine healthy and untreated living plants of *S. molesta* (type III, the biomass of three plants weighs approximately 10 g) were cultured in tap water in three plastic containers severing as three replications (14×15 cm, 0.68 L) with three plants each in a greenhouse (30° C. during the day time and 20° C. at night). The three plants in each of the three containers per treatment were sprayed with 10 mL NANOPURE™ water, 0.5% DYNE-AMIC®, or the experimental solution. Plant growth and survival status were documented and photographed in each treatment on day nine after the treatment. Pairwise comparisons for all treatments (including Control) in living biomass were made using Tukey test at alpha=0.05, which was done using SAS (SAS 9.4).

4-Hydroxybenzoic and 3,4-dihydroxybenzoic acids were also tested against Carolina mosquito fern (*Azolla caroliniana* Willd.) (family Azollaceae). Six containers (14×15 cm, 0.68 L) with full cover of *A. caroliniana* were included in the tests: two without any treatments as controls, two were sprayed with 10 mL 0.5% 4-hydroxybenzoic acid each, and the others were sprayed with 10 mL 0.5% 3,4-dihydroxybenzoic acid each. Plant growth and survival status were documented and photographed in each treatment on the fifth day after the treatment.

Results:

A summary of the results are found in Table 5. The combination of 4-hydroxybenzoic and 3,4-dihydroxybenzoic acids showed significant inhibitive activities against *S. molesta* plants in comparison with the control treatment with water only. Each of 4-hydroxybenzoic and 3,4-dihydroxybenzoic acids alone at 1% concentrations decreased the living biomass weight *S. molesta* by 85.5% and 76.5% nine days after the treatment, respectively, compared to the water control. The new growth from either treatment was type I only. 4-Hydroxybenzoic acid was found to be more effective than 3,4-dihydroxybenzoic acid and eliminated 100% of *S. molesta* plants at 2% concentrations. The mixture of 4-hydroxybenzoic and 3,4-dihydroxybenzoic acids was more effective than either of the compounds alone in the inhibition of *S. molesta*. The results suggest synergistic activity when the isolated compounds are combined. The mixture of 4-hydroxybenzoic and 3,4-dihydroxybenzoic acids at the ratio of 2:1 (w:w) killed 100% *S. molesta* plants at the total concentration 1% or higher. There was no new growth or induced plants observed during the experiment. Surfactant DYNE-AMIC® significantly improved the effectiveness of either isolate in the treatments. Ethylparaben had a similar role as the surfactant. 4-Hydroxybenzoic and 3,4-dihydroxybenzoic acids induced mutations of *S. molesta* at lower concentrations (not shown).

In the *Azolla* experiments, the plants in the control containers grew well. Both 4-hydroxybenzoic and 3,4-dihydroxybenzoic acids eliminated 100% of *A. caroliniana* at the 0.5% concentrations (not shown).

TABLE 5

Inhibition of giant *salvinia* (*Salvinia molesta*) by 4-hydroxybenzoic acid and 3,4-dihydroxybenzoic acid (means ± s.d. with the same letter do not differ significantly ($p < 0.05$))

| | Living Biomass (mean ± s.d.) (g) | | | | |
|---|---|---|---|---|---|
| | | Total Concentrations of the Testing Compound(s) | | | |
| Treatments | Water | 0.5% | 1.0% | 1.5% | 2.0% |
| Water | 29.8 ± 2.79 (a) | | | | |
| DYNE-AMIC® | | 20.6 ± 5.20 (ab) | | | |
| 4-Hydroxybenzoic acid | | 20.1 ± 0.12 (ab) | 4.3 ± 1.37 (def) | 2.3 ± 0.58 (ef) | 0 (f) |
| 3,4-Dihydroxybenzoic acid | | 17.1 ± 1.7 (bc) | 9.2 ± 7.9 (bcdef) | 14.3 ± 12.6 (bcd) | 5.8 ± 10.0 (cdef) |
| Ethylparaben | | 18.6 ± 2.37 (ab) | 18.7 ± 1.37 (ab) | 12.9 ± 4.29 (bcde) | 13.5 ± 0.70 (bcde |
| 4-Hydroxybenzoic acid & 3,4-dihydroxybenzoic acid | | 2.7 ± 2.46 (def) | 0 (f) | 0 (f) | 0 (f) |
| 3,4-Dihydroxybenzoic acid & DYNE-AMIC® | | 3.1 ± 0.93 (def) | 0.23 ± 0.13 (f) | 0 (f) | 0 (f) |
| 4-Hydroxybenzoic acid & DYNE-AMIC® | | 0.7 ± 0.36 (f) | 0.2 ± 0.15 (f) | 0.1 ± 0.17 (f) | 0 (f) |
| 3,4-Dihydroxybenzoic acid & ethylparaben | | 12.8 ± 8.23 (bcde) | 0.3 ± 0.46 (f) | 0 (f) | 0 (f) |

Example 15

Phytotoxic Analysis of 4-Hydroxybenzoic and 3,4-Dihydroxybenzoic Acids and their 14 Analogs on Giant Salvinia (*Salvinia molesta*)

General Experimental Procedure:

4-Hydroxybenzoic and 3,4-dihydroxybenzoic acids and 14 of their analogs were purchased commercially. Each of 16 compounds were prepared as 5 mL experimental solutions with NANOPURE™ water at 1% concentration. A total of 102 healthy and untreated living type III plants of *S. molesta* (approximately 10 g in fresh weight each) were cultured and tested in 17 plastic containers (23×23 cm, 2.37 L) with six plants in each container in a greenhouse (30° C. during the day time and 20° C. at night). The first container served as the controls without any treatment, the plants in each of the other 16 containers were treated by one of the 16 testing compounds, respectively. The plants in each container were randomly classified into two groups evenly. For each plant in the first group, 10 μL of 1% experimental solution was applied by pipet on the upper surface of each blade of the six pairs of large floating leaves close to the terminal bud. For each plant in the second group, 10 μL of 1% experimental solution was applied by pipet on the lower surface of each blade of the six pairs of large floating leaves close to the terminal bud. The leaf surfaces were examined for damage and analyzed 72 hrs after the treatments.

Results:

A summary of the results is shown in Table 6. At 72 hrs after the treatments, benzoic, 2-hydroxybenzoic, 4-hydroxybenzoic, 2,3-hydroxybenzoic, 2,4-hydroxybenzoic, and 3,4-dihydroxybenzoic acids showed strong phytotoxicity (>85% for upper surface application) against *S. molesta*. 3,5-dihydroxybenzoic, 2,4,6-trihydroxybenzoic, 3,4,5-trihydroxybenzoic, and nicotinic acids did not show any activities on either upper or lower leaf surface applications. The remaining six compounds had moderate activities.

[Structure: benzoic acid with R1–R5 substituents]

1 R₁ = H, R₂ = H, R₃ = H, R₄ = H, R₅ = H
2 R₁ = OH, R₂ = H, R₃ = H, R₄ = H, R₅ = H
3 R₁ = H, R₂ = OH, R₃ = H, R₄ = H, R₅ = H
4 R₁ = H, R₂ = H, R₃ = OH, R₄ = H, R₅ = H
5 R₁ = OH, R₂ = OH, R₃ = H, R₄ = H, R₅ = H
6 R₁ = OH, R₂ = H, R₃ = OH, R₄ = H, R₅ = H
7 R₁ = OH, R₂ = H, R₃ = H, R₄ = OH, R₅ = H
8 R₁ = OH, R₂ = H, R₃ = H, R₄ = H, R₅ = OH
9 R₁ = H, R₂ = OH, R₃ = OH, R₄ = H, R₅ = H
10 R₁ = H, R₂ = OH, R₃ = H, R₄ = OH, R₅ = H
11 R₁ = OH, R₂ = OH, R₃ = OH, R₄ = H, R₅ = H
12 R₁ = OH, R₂ = H, R₃ = OH, R₄ = H, R₅ = OH
13 R₁ = H, R₂ = OH, R₃ = OH, R₄ = OH, R₅ = H

14 [Structure: phenoxyacetic acid]

15 [Structure: isonicotinic acid]

16 [Structure: nicotinic acid]

Chemical Structure of 4-hydroxybenzoic acid and 3,4-dihydroxybenzoic acid and some of their related compounds in the tests.

TABLE 6

Inhibition of 4-hydroxybenzoic acid and 3,4-dihydroxybenzoic acid and some of their related compounds against *S. molesta*

| No. | Compound Name | Purity (%) | Inhibition (%) Upper leaf Application | Inhibition (%) Lower leaf Application |
|---|---|---|---|---|
| 1 | Benzoic acid | 99.5 | 88.89 | 100 |
| 2 | 2-Hydroxybenzoic acid | 99.5 | 100 | 100 |
| 3 | 3-Hydroxybenzoic acid | 99 | 36.12 | 66.67 |
| 4 | 4-Hydroxybenzoic acid | 99 | 100 | 100 |
| 5 | 2,3-Dihydroxybenzoic acid | 99 | 100 | 100 |
| 6 | 2,4-Dihydroxybenzoic acid | 99 | 100 | 72.23 |
| 7 | 2,5-Dihydroxybenzoic acid | 99 | 52.78 | 11.12 |
| 8 | 2,6-Dihydroxybenzoic acid | 98 | 44.44 | 25 |
| 9 | 3,4-dihydroxybenzoic acid | 97 | 86.12 | 72.23 |
| 10 | 3,5-Dihydroxybenzoic acid | 99 | 0 | 0 |
| 11 | 2,3,4-Trihydroxybenzoic acid | 98 | 44.45 | 11.12 |
| 12 | 2,4,6-Trihydroxybenzoic acid | 90 | 0 | 11.12 |
| 13 | 3,4,5-Trihydroxybenzoic acid | 99 | 0 | 0 |
| 14 | Phenoxyacetic acid | 98 | 77.78 | 16.67 |
| 15 | Isonicotinic acid | 98 | 44.45 | 33.33 |
| 16 | Nicotinic acid | 99.5 | 0 | 0 |

Example 16

Inhibition of Giant Salvinia (*Salvinia molesta*) and Some Associated Plant Species in the Field Tests by 4-Hydroxybenzoic and 3,4-Dihydroxybenzoic Acids General Experimental Procedure:

Field experiments were conducted in an isolated pond in east Texas, United States. The pond was infested with type III *S. molesta* plants that formed dense mats along the edge and type I and II plants floating on the water surface. 4-hydroxybenzoic and 3,4-dihydroxybenzoic acids were purchased from a commercial source (99.9%, HPLC analysis). 500 m² of *S. molesta* was treated with 50 L 0.5% 4-hydroxybenzoic acid mixed with 0.25% DAWN® dish soap and 500 m² of *S. molesta* was treated with 50 L 0.5% 3,4-dihydroxybenzoic acid mixed with 0.25% DAWN® dish soap by Solo 433 motorized backpack sprayer. Plant growth and survival status were documented through photographs and the living biomass was sampled 48 hrs after each treatment. The experimental species for selectivity tests were mainly common species associate with *S. molesta* or species growing in nearby habitats. The species included one fern species, Carolina mosquito fern (*A. caroliniana*), and 11 herbaceous invasive aquatic species of angiosperms (flowering plants), namely, water hyacinth (*Eichharnia crassipes* (Mart.) Solms) of the family Pontederiaceae, least duckweed (*Lemna minuta*) and Brazilian watermeal (*Wolffia brasillensis* Weddell) of the family Araceae, and *hydrilla* (*Hydrilla verticillata* (L.f.) Royle) of the family Hydrocharitaceae, alligator weed (*Alternanthera philoxeroides* Griseb.) of the family Amaranthaceae, knotweed (*Polygonum* sp.) and redvine (*Brunnichia ovata* Walter) of the family Polygonaceae, water primrose (*Ludwigia* sp.) of the family Onagraceae, cattail (*Typha latifolia* L.) of the family Typhaceae, proliferating bulrush (*Isolepis prolifera* (Rottb.) R. Br.) of the family Cyperaceae, and coontail (*Ceratophyllum demersum* L.) of the family Ceratophyllaceae and four woody plants, namely, baldcypress (*Taxodium distichum* (L.) Rich.) of the family Cupressaceae, loblolly pine (*Pinus taeda* L.) of the family Pinaceae, Chinese tallow (*T. sebifera*), and buttonbush (*Cephalanthus occidentalis* L.) of the family Rubiaceae. At least 30 plants for each of 12 herbaceous species and three seedlings of each of the four woody species were sprayed during the treatment of *S. molesta*.

Results:

>90% or >80% small *S. molesta* plants were found to be dead 48 h after the first treatment of either 0.5% 4-hydroxybenzoic acid or 3,4-dihydroxybenzoic acid with 0.25% soap. The new growths induced by these treatments were type I only. After the second treatments, all newly emerged type I plants were killed in either treatment. 100% of the type III *S. molesta* plants on the top layer of the dense mats were killed or severely injured by either compound within 48 hrs of the first treatment and some developed new growth of type II or III. These newly emerged *S. molesta* plants were killed or severely injured by either compound after the second treatment with some new growth of type I observed. However, none of the other species tested for selectivity except *A. caroliniana* were severely damaged or killed by 4-hydroxybenzoic or 3,4-dihydroxybenzoic acid after two foliar applications. These results suggest the specificity of the action of these compounds for giant *salvinia*.

Example 17

Inhibition of Giant *Salvinia* (*Salvinia molesta*) in the Field Tests by 4-Hydroxybenzoic and 3,4-Dihydroxybenzoic Acids General Experimental Procedure:

The field experiments were conducted in isolated ponds in east Texas, United States. The ponds are small (each were 200-500 m$^2$ in size) in the hardwood forests and each was fully covered with *S. molesta* plants and also included least duckweed (*L. minuta*) and Brazillan watermeal (*W. brasillensis*). The area was divided by plots, each plot had 50 m$^2$ in area including approximately 40 m$^2$ of type I and II *S. molesta* plants on the water surface and 10 m$^2$ of type III *S. molesta* plants on soils. Each plot, except a control plot, was treated with 20 L one of the following experimental solutions by Solo 433 motorized backpack sprayer: 0.5% 4-hydroxybenzoic acid, 0.5% 4-hydroxybenzoic acid mixed with 0.25% DAWN® dish soap, 0.5% 4-hydroxybenzoic acid and 0.25% 3,4-dihydroxybenzoic acid, 0.5% 4-hydroxybenzoic acid and 0.25% 3,4-dihydroxybenzoic acid with 0.25% DAWN® dish soap, and 0.25% DAWN® dish soap. Each test condition had three replicates. 12 days after the treatments, plant growth status was photographed and the plant survival rate was measured by three 1×1 m random sample plots for floating plants on the water surface and two samples in 1×1 m random sample plots for plants on soils. Pairwise comparisons for all treatments (including Control) for living biomass were made using Tukey test at alpha=0.05, which was done using SAS (SAS 9.4).

Results:

A summary of the results are found in Table 7. 96.2% and 91.3% of *S. molesta* plants survived in the control plot on the water surface and the soils on the day 12 after the treatments, respectively. The type I plants continued to grow as type I form or a few became type II during the 12 day experimental period. Most of the type II plants grew but stayed in type II with some in type III. The type III plants grew only type III in the control plot. 34.7% and 14.3% of the *S. molesta* plants survived on the water surface and soils, respectively, following the treatment of 0.5% 4-hydroxybenzoic acid. Induced new growth in this treatment was primarily type I and II. 0.5% 4-Hydroxybenzoic with 0.25% DAWN® dish soap had similar effects on *S. molesta* survivals as treatment with only 0.5% 4-hydroxybenzoic acid. However, only 18.9% and 4.18% of the *S. molesta* plants survived on the water surface and soils, respectively, following the treatment of a combination of 0.5% 4-hydroxybenzoic acid and 0.25% 3,4-dihydroxybenzoic acid mixed with 0.25% DAWN® dish soap. The new growth following this treatment was primarily type I. In general, the two compounds or their combination killed *S. molesta* plants on the soils more effectively than those floating on water surface. 100% of the treated plants were dead in some spots within 48 h after treatment. 0.25% DAWN® dish soap alone had no significant impacts on *S. molesta* growth.

TABLE 7

4-Hydroxybenzoic and 3,4-dihydroxybenzoic acids, two endocidal compounds effectively inhibited *Salvinia molesta* by the end of the 12 days after the first treatment in the field tests (means ± s.d. with the same letter do not differ significantly ($p < 0.05$)

| | % of Living Biomass/Total Biomass (mean ± s.d.) | |
|---|---|---|
| Treatments | Type I and II Plants on Water Surface | Type III Plants on Soils |
| Control | 96.2 ± 1.38 (a) | 91.3 ± 0.71 (a) |
| 0.25% DAWN ® soap | 89.2 ± 0.75 (a) | 84.2 ± 5.87 (a) |
| 0.5% 4-Hydroxybenzoic acid | 34.7 ± 6.81 (b) | 14.3 ± 1.06 (bc) |
| 0.5% 4-Hydroxybenzoic acid with 0.25% DAWN ® soap | 35.8 ± 4.55 (b) | 15.5 ± 0.65 (b) |
| 0.5% 4-Hydroxybenzoic acid and 0.25% 3,4-dihydroxybenzoic acid with 0.25% DAWN ® soap | 18.9 ± 4.91 (c) | 4.18 ± 2.52 (c) |

REFERENCES

PP11,959
WO 02/42428
U.S. application Ser. No. 14/889,184
Abad J. M., Bermejo P. (2001). Bioactive natyral products from marine sources. *Studies in Natural Products Chemistry*. Atta-ur-Rahman. Oxford, Elsevier. 25: 683-756.
Ali, B. H., N. AlWabel, et al. (2005). "Phytochemical, pharmacological and toxicological aspects of *Hibiscus sabdariffa* L.: a review." *Phytotherapy Research*. 19(5): 369-375.

Asao, T., K. Hasegawa, et al. (2003). "Autotoxicity of root exudates from taro." *Sci. Hort.* 97(3-4): 389-396.

Asao, T., H. Kitazawa, et al. (2004). "Search of autotoxic substances in some leaf vegetables." *J. Jpn. Soc. Hortic. Sci.* 73(3): 247-249.

Baldwin I. T. (2001). "An ecologically motivated analysis of plant-herbivore interactions in native tobacco." *Plant Physiology.* 127(4): 1449-1458.

Baldwin I. T., Callahan P. (1993). "Autotoxicity and chemical defense: nicotine accumulation and carbon gain in solanaceous plants." *Oecologia.* 94: 534-541.

Bennett R. N., Wallsgrove R. M. (1994). "Secondary metabolites in plant defence mechanisms." *New Physiology.* 127: 617-633.

Croteau R., Kutchan T. M., et al. (2000). Natural products (secondary metabolites) *Biochemistry and Molecular Biology of Plants.* B. Butchanan, W. Gruissem and R. Jones, *American Society of Plant Physiologists.* 1250-1318.

Dai, L. Q. (2012). Studies on the interaction of autotixic chemicals of taizishen and the microbes in rhizosphere soils. Proceeding of the 4$^{th}$ Symposium of the Committee of Resource ecology of Chinese Traditional Medcine of the Ecological Scoeity of China and the 11$^{th}$ Symposium of Committee of Traditional Chinese Medicine.

Davies J. (1992). Introduction. *Secondary metabolites: Their Function and Evolution.* D. J. Chadwick and J. Whelan, John Wiley & Sons Ltd: 1-2.

Dixon R. A. (2001). "Natural products and plant diseas resistance." *Nature.* 411: 843-847.

Ellnain-Wojtaszek, M. (1997). "Phenolic acids from *Ginkgo biloba* L. Part II. Quantitative analysis of free and liberated by hydrolysis phenolic acids." *Acta Poloniae Pharmaceutica.* 54(3): 229-232.

Ffolliott P. F., Brooks K. N., et al. (1995). *Dryland Forestry Planning and Management*, New York, Chichester, Brisbane, Toronto, Singapore, John Wiley & Sons, Inc.

Gog L., Berenbaum M. R., et al. (2005). "Autotoxic effects of essential oils on photosynthesis in parsley, parsnip, and rough lemon." *Chemoecology.* 15: 115-119.

Herrmann, K. (1989). "Occurrence and content of hydroxycinnamic and hydroxybenzoic acid compounds in foods." *Critical Reviews in Food Science and Nutrition.* 28(4): 315-347.

Huang, L. F., L. X. Song, et al. (2013). "Plant-soil feedbacks and soil sickness: from mechanisms to application in agriculture." *Journal of Chemical Ecology.* 39: 232-242.

Huang, X., Z. Bie, et al. (2010). "Identification of autotoxins in rhizosphere soils under the continuous cropping of cowpea." *Allelopath. J* 25(2): 383-392.

Hudson, E. A., P. A. Dinh, et al. (2000). "Characterization of potentially chemopreventive phenols in extracts of brown rice that inhibit the growth of human breast and colon cancer cells." *Cancer Epidemiology Biomarkers and Prevention.* 9(11): 1163-1170.

Ibáñez A. J., Scharte J., et al. (2010). "Rapid metabolic profiling of *Nicotiana tabacum* defence responses against *Phytophthora nicotianae* using direct infrared laser desorption ionization mass spectrometry and principal component analysis." *Plant Methods.* 6: 14.

Jurgenliemk, G. and A. Nahrstedt (2002). "Phenolic compounds from *Hypericum perforatum*." *Planta Medica.* 68(1): 88-91.

Kakkar, S. and S. Bais (2014). "A review on protocatechuic acid and its pharmacological potential." *ISRN Pharmacology.* 2014: 1-9.

Kayano, S. I., H. Kikuzaki, et al. (2002). "Antioxidant activity of prune (*Prunus domestica* L.) constituents and a new synergist." *Journal of Agricultural and Food Chemistry.* 50(13): 3708-3712.

Kim, Y. O., J. D. Johnson, et al. (2005). "Phytotoxic effects and chemical analysis of leaf extracts from three Phytolaccaceae species in South Korea." *J. Chem. Ecol.* 31(5): 1175-1186.

Kliebenstein D. J. (2004). "Secondary metabolites and plant/environment interactions: a view through *Arabidopsis thaliana* tinged glasses." *Plant, Cell & Environment.* 27(6): 675-684.

Li, P., X. Q. Wang, et al. (1993). "Highperformance liquid chromatographic determination of phenolic acids in fruits and vegetables." *Biomedical and Environmental Sciences.* 6(4): 389-398.

Li, S. (2002). A system for increasing the production of indole and quinoline alkaloids, particularly camptothecins and related compounds, from plants. R.O. China Invention. 162720.

Li S. (2014). "Taxonomy of *Camptotheca* Decaisne." *Pharmaceutical Crops.* 5 (Suppl 2: M2): 89-99.

Li, S., P. Wang, et al. (2013). "Cytotoxic compounds from invasive giant salvinia (*Salvinia molesta*) against human tumor cells." *Bioorganic & Medicinal Chemistry Letters.* 23: 6682-6687.

Li S. Y., Wang P., et al. (2010). "Induced endogenous autotoxicity in *Camptotheca*." *Frontiers in Bioscience.* E2: 1196-1210.

Li S. Y., Yi Y. J., et al. (2002). "Camptothecin accumulation and variation in *Camptotheca* Decaisne." *Planta Medica.* 68(11): 1010-1016.

Li S. Y., Zhang Z. Z., et al. (2014). "Trichome management to enhance camptothecins in *Camptotheca* Decaisne." *Pharm. Crops.* 5(Suppl 2: M8): 146-162.

Li, Z. F. (2012). Synergistic effect of autotoxins and phytopathogenic fungi on the pathogenicity to rehmannia in consecutive monoculture system, *Fujian Univ. Agric. For.*

Li, Z. F., Y. Q. Yang, et al. (2012). "Identification of autotoxic compounds in fibrous roots of Rehmannia (*Rehmannia glutinosa* Libosch)." *PLoS ONE.* 7(1): e28806.

Liu, A. M., S. Xu, et al. (2011). "Effects of phenolic acids and amino acid on the growth of *Fusarium* Oxysporium f sp. *niveum*." *Huibei Agric. Sci.* 50(20): 4180-4184.

Liu, C. L., J. M. Wang, et al. (2002). "In vivo protective effect of protocatechuic acid on tert-butyl hydroperoxide-induced rat hepatotoxicity." *Food and Chemical Toxicology.* 40(5): 635-641.

Liu, P., X. H. Gao, et al. (2012). "Interactive effects of three kinds of phenolic acids on peanut germination and soil microbes." *Acta Agric. Jiangxi.* 24(8): 85-87, 93.

Mandal, S. M., D. Chakraborty, et al. (2010). "Phenolic acids act as signaling molecules in plant-microbe symbioses." *Plant Signaling & Behavior.* 5(4): 359-368.

Masella, R., A. Cantafora, et al. (1999). "Antioxidant activity of 3,4-DHPEA-EA and protocatecuic acid: a comparative assessment with other olive oil biophenols." *Redox Report.* 4(3): 113-121.

Mattilla, P. and J. Hellstrom (2007). "Phenolic acids in potatoes, vegetables, and some of their products." *Journal of Food Composition and Analysis.* 20(3-4): 152-160.

Moorman, T. B., J. M. Becerril, et al. (1992). "Production of hydroxybenzoic acids by *Bradyrhizobium japonicum* strains after treatment with glyphosate." *Journal of Agricultural and Food Chemistry.* 40: 289-293.

Netzly, D. H., J. L. Riopel, et al. (1988). "Germination stimulants of witchweed (*Striga asiatica*) from hydrophobic root exudate of sorghum (*Sorghum bicolor*)." *Weed Science.* 36(441-446): 36.

Pacheco-Palencia, L. A., S. Mertens-Talcott, et al. (2008). "Chemical composition, antioxidant properties, and thermal stability of a phytochemical enriched oil from Acai (*Euterpe oleracea* Mart.)." *Journal of Agricultural and Food Chemistry.* 56(12): 4631-4636.

Reisman-Berman O., Kigel J., et al. (1989). "short soaking in water inhibits germination of *Datura ferox* L. and *D. stramonium* L. seeds" *Weeds Research.* 29: 357-363.

Rhoaders H. (2015) How to soak seeds before planting and the reasons for soaking seeds.

Sang, S., S. Lapsley, et al. (2002). "Antioxidative phenolic compounds isolated from almond skins (*Prunus amygdalus* Batsch)." *Journal of Agricultural and Food Chemistry.* 50(8): 2459-2463.

Singh, N. and P. S. Rajini (2008). "Antioxidant-mediated protective effect of potato peel extract in erythrocytes against oxidative damage." *Chemico-Biological Interactions.* 173(2): 97-104.

Sirikantaramas S., Yamazaki M., et al. (2008). "Mechanism of resistance to self-produced toxic secondary metabolites in plants." *Phytochemistry Reviews.* 7: 467-477.

Sirikantaramas S., Yamazaki M., et al. (2008). "Mutations in topisomerase I as a self-resistance mechanism coevolved with the production of the anticancer alkaloid camptothecin in plants." *PNAS.* 105: 6782-6786.

Wang, J. C. (1996). "DNA topoisomerases." *Annual Review of Biochemistry.* 65: 635-692.

Wang, M. S., M. Li, et al. (2014). "Effect of phenolic acid on the root growth and photosynthetic characteristics of tobacco seedlingcharacteristi to bacco seedling." *Guangdong Agri. Sci.* (2): 14-18.

Williams D. H., Stone M. J., et al. (1989). "Why are secondary metabolites (natural products) biosynthesized?" *Journal of Natural Products.* 52(6): 1189-1208.

Wink M. (2003). "Evolution of secondary metabolites from an ecological and molecular phylogenetic perspective." *Phytochemistry.* 64: 3-19.

Wu, H. C. (2006). Improving in vitro propagation of rooting in Protea cynaroides L. (king protea) and the roles of starch and phenolic compounds in the rooting of cuttings. PhD, University of Pretoria.

Wu, H. C., E. S. du Toit, et al. (2007). "The phenolic, 3,4-dihydroxybenoic acid, is an endogenous regulator of rooting in Protea cynaroides." *Plant Growth Regulation.* 52: 207-215.

Young J. A., Young C. G. (1992). *Seeds of Woody Plants in North America.* London, Timber Press.

Yu, H. Y., H. B. Liang, et al. (2014). "Effects of allelochemicals from tobacco root exudates on seed germination and seedling growth of tobacco." *Allelopath J.* 33(1): 107-120.

Yu, H. Y., G. M. Shen, et al. (2014). "The changes and degradation of tobacco root exudates in tobacco field with continuous cropping." *Chinese Tobacco Sci.* 35(1): 43-47.

Zeng, R. S. (2014). "Allelopathy—The Solution is Indirect." *Journal of Chemical Ecology.* 40: 515-516.

Zhang, K., T. Xu, et al. (2013). "Phenoli acid in *Nicotiana* tobacco L. root exudate and their autotoxicity effects." *Southwest China Agric. Sci.* 26(6): 2552-2557.

Zhou, X. and F. Wu (2012). "p-Coumaric ccid influenced cucumber rhizosphere soil microbial communities and the growth of *Fusarium oxysporum* fsp. cucumerinum Owen." *PLOS ONE.* 7(10): e48288.

Zhou, X. G., C. B. Yu, et al. (2012). "Responses of soil microbial communities in the rhizosphere of cucumber (*Cucumis sativus* L.) to exogenously applied p-hydroxybenzoic acid." *J. Chem. Ecol.* 38: 975-983.

What is claimed is:

1. A method of killing a plant of a first species, the method comprising contacting the plant of the first species with a composition comprising:
   a preservative not derived from the first species; and
   0.1 wt. % or more of an endocide to the first species, wherein:
   the first species is a species in the order of Salviniales and the endocide is 4 hydroxybenzoic acid or 3,4-dihydroxybenzoic acid, and wherein contacting the plant with the endocide to the first species kills the plant.

2. The method of claim 1, wherein the composition contacts a propagule or other propagative tissue of the plant of the first species.

3. The method of claim 1, wherein the composition comprises 0.25% or more by weight of the endocide.

4. The method of claim 1, wherein the method comprises soaking a propagule or other propagative tissue of the plant of the first species in the endocide or a composition comprising the endocide for at least 7 days, 10 days, 2 weeks, 4 weeks, 6 weeks, 8 weeks, 10 weeks, or 12 weeks.

5. The method of claim 2, wherein the plant of the first species in the order of Salviniales is *S. canadensis*.

6. The method of claim 1, wherein the plant of the first species is *Azolla caroliniana*.

7. The method of claim 1, wherein the endocide is 3,4-dihydroxybenzoic acid.

8. The method of claim 1, wherein the composition is applied topically to the plant of the first species, applied to a trichome of the plant of the first species, sprayed on the plant of the first species, spread around the plant of the first species, and/or dissolved in water surrounding the plant of the first species.

9. The method of claim 1, wherein the endocide is 4-hydroxybenzoic acid.

10. The method of claim 1, comprising contacting the plant of the first species with a secondary agent and/or at least two endocides, derivatives thereof, and/or analogues thereof.

11. The method of claim 1, wherein the species in the order of Salviniales is *Salvinia molesta*.

12. The method of claim 1, wherein the composition comprises both 4-hydroxybenzoic acid and 3,4-dihydroxybenzoic.

13. The method of claim 1, wherein the composition comprises 0.125% or more by weight of the endocide.

14. The method of claim 1, wherein the composition comprises 0.5% or more by weight of the endocide.

* * * * *

UNITED STATES PATENT AND TRADEMARK OFFICE
CERTIFICATE OF CORRECTION

PATENT NO. : 10,694,692 B2
APPLICATION NO. : 15/775570
DATED : June 30, 2020
INVENTOR(S) : Shiyou Li et al.

It is certified that error appears in the above-identified patent and that said Letters Patent is hereby corrected as shown below:

On the Title Page

In Item (56) References Cited, OTHER PUBLICATIONS, Line 18, replace "ElseVier" with --Elsevier--.

In Item (56) References Cited, OTHER PUBLICATIONS, Line 35, replace "Oligins" with --Origins--.

On the second page in Item (56) References Cited, OTHER PUBLICATIONS, left column, Line 11, replace "Part 11" with --Part II--.

On the second page in Item (56) References Cited, OTHER PUBLICATIONS, right column, Line 4, replace "Synergistic Rehmannia in Consecutive Effect of Autotoxins and Phytopathogenic Fungi on the Pathogenicity to Monoculture System" with --Synergistic Effect of Autotoxins and Phytopathogenic Fungi on the Pathogenicity to Rehmannia in Consecutive Monoculture System--.

On the second page in Item (56) References Cited, OTHER PUBLICATIONS, right column, Line 8, replace ""SaIVinia(Sa1Vinia" with --Salvinia (Salvinia--.

Signed and Sealed this
Eighteenth Day of August, 2020

Andrei Iancu
*Director of the United States Patent and Trademark Office*